(12) United States Patent
Bullis

(10) Patent No.: US 6,876,597 B2
(45) Date of Patent: Apr. 5, 2005

(54) CHANNELED WAVEFIELD TRANSFORMER

(76) Inventor: James K. Bullis, 1155 Pimento Ave., Sunnyvale, CA (US) 94087

( * ) Notice: Subject to any disclaimer, the term of this patent is extended or adjusted under 35 U.S.C. 154(b) by 623 days.

(21) Appl. No.: 10/060,591

(22) Filed: Jan. 30, 2002

(65) Prior Publication Data

US 2003/0140702 A1 Jul. 31, 2003

(51) Int. Cl.$^7$ .......................... G01N 29/00; G03B 42/06
(52) U.S. Cl. .......................................................... 367/11
(58) Field of Search ................................ 367/7, 11, 10, 367/103, 130; 600/437, 442; 348/81, 163, 16, 162, 164; 73/602, 609

(56) References Cited

U.S. PATENT DOCUMENTS

| 4,650,279 A | 3/1987 | Magee ........................ 385/116 |
| 5,428,999 A | 7/1995 | Fink ............................. 73/602 |
| 6,291,927 B1 | 9/2001 | Percin et al. ................ 310/324 |
| 6,524,248 B1 * | 2/2003 | Bullis .......................... 600/437 |
| 2001/0044995 A1 | 11/2001 | Tezuka ....................... 29/25.35 |

* cited by examiner

Primary Examiner—Daniel Pihulic

(57) ABSTRACT

The channeled wavefield transformer enables multi-dimensional wavefield signal processing which leads to significant expansion of the engineering field of electronic signal processing. The term "wavefield" is used to indicate one or more waves that operate in at least two dimensions of space where spatial form of a wave can be represented by a wavefront that is a surface of points of equal phase. This transformer produces an output wavefield in a clear medium in response to an arbitrary input wavefield. This is carried out using multiple channels that connect input sensing devices to respective output transmitting devices, through general electrical or optical networks. The input devices are arranged along an input surface and the output transmitting devices are arranged along an output surface. An output wavefield emerges from the output surface to propagate in an output wavefield space.

33 Claims, 22 Drawing Sheets

(a)

(b)

(a) (b) (c)

(a)

(b)

CHANNELED WAVEFIELD TRANSFORMER

CROSS REFERENCE TO RELATED APPLICATIONS

This invention uses a component of U.S. Pat. No. 6,524,248 Bullis (Feb 2002).

BACKGROUND OF THE INVENTION

This patent document contains material that is subject to copyright protection. Facsimile reproduction is allowed of the patent document or the patent disclosure as it appears in the Patent and Trademark Office patent file or records as allowed by U.S. patent law, but otherwise all copyright rights are reserved.

This invention relates to receiving a radiating input wavefield that propagates in a medium and transmitting a radiating output wavefield in a medium. Example applications in the field of the invention include general optical devices, radar systems, ultrasonic medical imaging systems, ultrasonic industrial inspection, seismic prospecting, and sonar. High power applications, where waves modifiy materials, are included in this field as well as low power applications, where waves pass through a medium without modifying the materials.

A wavefield operates in space and time. Typical use of this term is in connection with waves in three dimensional space where a quantity such as magnitude of an electric field varies over both space and time. Describing such a wavefield involves three dimensions of space as well as time. In this document the term "wavefield" is used to indicate one or more wavefields that operate in at least two dimensions of space. Where a wavefield has a spatial form that can be represented by a wavefront that is a surface of points of equal phase, that wavefield is spatially coherent. Waves naturally propagate from a point source in a clear medium as coherent wavefields that can be represented by spherical wavefronts.

A restricted wave is a wave on a wire or in a waveguide where the electric field varies along its transmission path as a function of time. Describing this restricted wave involves one dimension of space and one of time, but often the space dimension can be ignored. Such a restricted wave is here called a signal in a channel. A wavefield may also be restricted to a planar surface such that only two dimensions of space and one of time can fully describe its operation.

A transformer is a standard device in electrical and electronic systems. Electrical power systems use transformers to modify voltage for power distribution where there is an input voltage and an output voltage. Another use of the transformer is to match impedances such that maximum power is transferred. Such transformers are passive devices where output power is no more than input power. Such standard transformer applications relate to electrical variations as a function of time only. The most common transformer produces an output waveform in response to an input waveform in accordance with the ratio of turns of wire in the secondary winding to turns of wire in the primary winding. This rule is applied for an arbitrary input waveform that is applied to the input point. For a linear transformer device the principle of superposition applies such that two waveforms that are combined at the input will both be subjected to the same transformation process in parallel. If the input waveforms are simultaneous, then the parallel transformation processes will be simultaneous.

Transformers operate in reverse. A discussion about operation in one direction implies a corresponding operation in the reverse. This is generally assumed for all devices discussed in this document, with appropriate modification of device details where necessary. For example, transmit operations of radars generally utilize much of the same equipment as receive operations, but where transmit and receive functions are involved there is a separation of these functions.

Optical devices have a general purpose of modifying optical waves. Counterparts are known in prior arts of radar, sonar, and ultrasound. Such a purpose is accomplished where input wavefields are continuously sampled over a surface. Mirrors, lenses, prisms, gratings, screens, and apertures in screens are examples. All of these devices carry out a transformation of an input wavefield. For an input wavefield that is a composite of component wavefields, transformations take place for all component waves as parallel processes. Except for some high power wavefield cases, these devices usually operate as linear devices so the principle of superposition applies such that waves from multiple sources that simultaneously arrive at an input surface undergo transformations that are simultaneous, without significant mutual effects. Lenses are most commonly associated with optical waves, but ultrasonic lenses and radar lenses accomplish similar functions through their operation as refractive devices.

Signal processing is a field of electronic engineering with counterparts in physics, including optics. The electronic category has expanded greatly with the availability of special digital signal processing (DSP) integrated circuits. The general field still includes many analog devices such as amplifiers, filters, mixers. Switches are more for the purpose of modifying a configuration rather than changing the form of a signal. Delay devices and phase shifters also operate without modifying form of the signal. The general field is mostly organized much like operation of the transformer. A network is typically defined that has a transfer function that defines the output response at an output point to an input response at an input point. Much of this field is based on the capability of transistors to amplify signals. Amplifiers are a form of active device. An active device causes active signal modification where an output signal carries more power than the corresponding input signal.

Great strides have recently been made in electronic signal processing, but in spite of this the field of optical signal processing continues to have major advantages in processing speed since a propagating wavefield represents many processes that are painstakingly slow in electronic signal processing. Many electronic channels are needed to do things that are carried out by a single focused wavefield. For example, an optical processor that is a simple lens is all that is required to cause such a focused wavefield that delays and sums a continuous wave that is equivalent to a very large number of channels. However, a lens is strictly a passive device without the flexibility of electronic devices to include active devices that increase power in a signal. A lens is also fixed after it is constructed where electronic processes can be readily varied. Lenses have generally been used for direct processing of wavefields where the form of energy is essentially the same throughout the process. For example, light waves vary only in speed as they enter the lens, travel through lens material, and exit the lens. Lenses have also been used for indirect wavefield processing where form of the wave energy is modified prior to wavefield processing. Acoustic holography is an example of this latter mode, where form of wave energy is interchanged from acoustic waves to light waves.

A previous patent U.S. Pat. No. 6,524,248 B1 Bullis (Febuary 2003) disclosed an aberration correction system that included a forward propagation device that carried out a wavefield transformation process where an input wavefield is transformed into an output wavefield using a one-to-one mapping process. The mapping was done with many parallel channels that conveyed signals from an input surface to an output surface. This caused an output wavefield that included component wavefields, one of which was a collimated wave and others were spherical waves. Differences in propagation of such components enabled separation of distortion signals arising at multiple source points from an intended signal arising at an intended focus point. The multiple distortion signals were separated and evaluated to determine correction signals that operate in parallel. This disclosure was written with the purpose specifying an aberration correction device and did not develop the general purpose nature of this transformation device.

U.S. Pat. No. 5,428,999 Fink (July 1995) disclosed a time reversal mirror that carried out a reverse propagation process in an inhomogeneous medium for the purpose of compensating for wave speed irregularities. Received signals were stored and retransmitted from the same devices that were used to receive the signals.

While much of the field of electronic signal processing addresses the topic of point to point transforming of signal waveforms, the task of receiving wavefield signals occasionally arises. Such operations are sometimes called spatial signal processing. For reception of input wavefield signals, the wavefields are typically converted to time domain signals at sample points in space that are on the surface of an array, and then conveyed in electronic channels to an electronic summing point. The channels are configured such that, for an input wavefield that originates at a source point in space, a signal at the summing is a response to a signal at that source point. The process of selecting different source points is accomplished by adjusting time delays in the channels. Sequential operations with different time delay sets allows sequential sensing of wavefield components from multiple source points. This type of signal processing is sequential beamforming. Parallel operations are possible where multiple summing points are arranged, where each summing point has its own set of channels from the sample points. Each of the multiple summing points produces a signal and the signals are responses to respective wavefield source points. Such electronic processing carries out a limited type of lens function, with more flexibility in varying configurations. Where input and output surfaces are shaped glass, there is obviously no opportunity for variation after fabrication. Where input and output surfaces are transducer arrays, the shapes are also difficult to vary but the electronic processing flexibility helps to restore some flexibility.

A device that operates similarly to the sequential beamforming process is called a fiber optic lens, as disclosed in U.S. Pat. No. 4,650,279 Magee (March 1987). The equivalent of the summing point is a fixed focus point that is on the lens axis. This special form of lens utilizes optical fibers to connect input points on an input aperture to output points on output aperture, and is thus limited to waves that can be sampled by and conveyed in an optical fiber. In this invention, input wavefronts representing a wave from a fixed source point that is at a fixed direction are made to converge to a receiving point. In doing so, input wavefronts are transformed into curved wavefronts that represent a focused wave that concentrates energy at the receiving point. While this device utilizes a wavefront transformation effect, its purpose is to reduce the wavefield to a signal at a single point. The specification directs that the point where energy is concentrated is set in fabrication of the device. In a first embodiment, the source point is also set in fabrication.

However, U.S. Pat. No. 4,650,279 Magee (March 1987) also provides for adjustments that can be made immediately prior to receiving operation. These adjustments are for changing effective pointing angle of the device to sense a source point in a different direction. After adjustment the spatial form of the input wavefield and the spatial form of the output wavefield are fully specified. The only unknown is the time function of the wavefield signal.

Because U.S. Pat. No. 4,650,279 Magee (March 1987) is designed for a limited purpose telescope application, it specifies contrary to concepts of operating on wavefronts having arbitrary spatial form and of parallel operation for multiple input wavefields. It also specifies contrary to the concept of simultaneously focusing wavefields from multiple points in space onto a focal plane. These concepts are among known functions of optical lenses that are beyond reach of this limited invention. This is evidenced by specification of a single receiving point on the device axis and by a pre-set source point location.

The fiber optic lens of U.S. Pat. No. 4,650,279 Magee (March 1987) is also limited as a passive device. Even though active methods are an obvious part of devices to change the length of the fibers, the signal in the fibers neither increases in power nor significantly changes in form as it passes through the extended fiber.

Radar lenses are also known but these have similarly limited purpose. Barton provides a survey discussion of such radar lenses in Skolnik (editor), *Radar Handbook*, McGraw-Hill, Inc., 1970, pp 10-19–10-24. While radar lenses operate on the basis of refraction effects, configurations are discussed in this reference where a lens material is compartmented by an arrangement of metal surfaces or a lens effect is arranged by a waveguide effect of metal surfaces. Such compartments operate with wavefield signals in the upper range of radar frequencies where waveguides are effective. Wavefields arrive at an input surface where they enter the compartments that convey the signals to an output surface. The compartments confine a portion of the input wave energy and deliver it to an output point. Barton discusses various arrangements where, like the above discussed fiber optic lens, the radar lens is steered in direction such that a single focus position on the lens axis is maintained. An alternative is a method of steering that is a sequential motion of a focus point over a focal surface. These methods are thus specified for wavefields of pre-determined spatial form. They also preclude parallel operation for waves from multiple sources. Because it is natural for radar systems to rely on transmit beams and receive beams, it is usual practice to receive only for points illuminated, and thus multiple simultaneous receive channels are uncommon. Thus discussions of radar lenses naturally preclude simultaneous focusing of wavefields from multiple sources on a focal surface. As with the fiber optic lens, radar lens devices are fundamentally passive devices.

In radar there are some devices called lenses that are actually electronic beamforming devices. Such misnamed lenses utilize channels to convey sampled signals from an input wavefield directly to summing points by electronic transmission devices, without use of a secondary, radiating output wavefield. Knittel describes such a device in Brookner (editor), *Radar Technology*, Artech House, Inc., 1977. pp 300–301.

Transducers are devices that change the form of energy through a conversion process. These include such devices as piezoelectric sensors that change pressure waves into electrical signals. Arrays of transducers are known for the purpose of spatially sampling a wave over an aperture surface. Typically, electronic signal processing carries out the necessary functions to convert the wave samples into an electronic signal. Definitions become less clear where waves are electromagnetic processes in free space and signals are electromagnetic processes in somewhat confined space, as in a waveguide. However, a waveguide opening is a form of transducer that simply channels wave energy from free space into the waveguide. Reciprocal processes are understood to be similar. The fiber optic lens as disclosed in U.S. Pat. No. 4,650,279 Magee (March 1987) involves light entering the optical fibers and being then confined to the fibers similar to the way lower frequency electromagnetic waves entering waveguides. In the same sense, entry and exit from an optical fiber can be considered as a transducer operation.

Arrays of transducers are widely used. Medical imaging is an area that utilizes ultrasonic transducer arrays. Most of these involve transducers that are arranged along a line that is either a straight line or a curved path. Transducers along such a line can have width such that the array has substantial area. Companies manufacturing such arrays have capabilities of varying the number of elements, size and shape of elements, and surface forms. An example is Acoustic Imaging Technologies, Inc. Some arrays involve transducers that are distributed over two dimensions to form a matrix surface. Representative two dimensional arrays are disclosed by U.S. Pat. No. 6,291,927 B1 Percin et al. (September 2001) and 2001/0044995A1 Tezuka (November 2001). These are both limited to planar surfaces. They also involve construction of the array surface as an assembly. Electrical connections are then attached by various methods to form a working system. 2001/0044995A1 Tezuka (November 2001) provides for layers that contain rows of connecting wires, and the layers are assembled with backing material prior to attaching a shell of piezoelectric material that is then cut into individual transducers.

Surface acoustic wave (SAW) devices use a form of ultrasonic waves for signal processing of electrical signals. One such use is for implementing delay lines where acoustic wave devices provide respective delays for signal channels. Appropriately delayed signals are combined electrically, using analog or digital techniques.

Bulk acoustic wave (BAW) devices use another form of ultrasonic waves for carrying out Fourier transform operations on time based signals.

The process of receiving wave signals with an array of transducers, summing signals from that array to form a signal and and distributing and transmitting that signal from a second array of transducers is a common practice in communications. This would be generally referred to as a relay process. A single channel communicates from the input system to the output system. Such a process is not a one-to-one mapping, rather a signal at a sample point on an input array becomes part of each signal at all sample points on the output array.

Common television maps signals from a focal plane in a television camera to pixels on a television receiver. In these systems wavefronts arriving at the camera lens are focused at the camera focal plane such that there is not a phase relationship between signals at the various points on the camera focal plane. Such signals are not spatially coherent. The focal plane sensor operates as a power detector such that the mapping does not carry phase information forward. Signals that are the result of power detection eliminate phase information and are, thus, non-coherent signals.

While there is an extensive background for the present invention, no prior art has effectively captured the generality of optical devices and their counterparts in combination with the generality of electronic signal processing.

SUMMARY OF THE INVENTION

The channeled wavefield transformer was originally developed for the purpose of processing ultrasonic wavefield signals with the spatial processing efficiency of optical devices. Spatial processing involves operations on general wavefields having spatially coherent wavefield components. For such components, wavefronts characterize points of equal phase over a mathematically defined, spatial surface. While the functions of the wavefield transformer can be imitated in electronic devices such as a digital computer, processes that require lengthy computations can be achieved in the time of propagation over a short path using wavefield processing. A channel system was the basis of this transformer, where electronic system flexibility was incorporated into a lens like device. It then was noted that this device had great flexibility that would be useful in optical processing or any other field involved with wavefields. Beyond ultrasonic systems, it enables a great range of products ranging from coherent television that operates directly into the eye to high power industrial devices.

The channeled wavefield transformer is a general purpose signal processing device that uses a pair of arrays of discrete transducers to cause spatial processing of wavefield signals, comparable to processing with optical devices. This invention transforms an input wavefield that propagates in a first medium into an output wavefield that propagates in a uniform second medium. The pair of arrays implements a wave mapping process where wavefield variations occurring at points on an input surface are transformed into wavefield variations at points on an output surface. This is a one-to-one mapping, where signals received by elements of an input array are mapped to respective elements of an output array. This is carried out through respective signal mapping channels. A plurality of such signal mapping channels is required. As signals travel through the channels, coherent relationships are controlled for signals across all channels.

An example system involves a pair of ultrasonic arrays that are constructed using a stacking process where transducer modules are stacked to form the desired surface shapes. The channels connecting the ultrasonic arrays operate with sufficient speed that propagation time in these channels is negligible to the wavefield transformation effect.

Both the input wavefield and the output wavefield are unrestricted as to type of propagating energy form. The input wavefield can be a different form of energy from the output wavefield. Laws of scaling make this device useful at any wavelength including seismic waves up to optical waves. Input and output wavefields can operate in the same or separate media and such media can be anything from an ocean volume to a tiny container of water to a flat surface wave device, and anything else that can be arranged.

Special advantages are added where devices that provide active signal modification are inserted in the signal mapping channels. Other devices known to the field of electronic signal processing may also be inserted in the channels. Signals may be discrete time sampled signals as well as continuous signals. However, a major advantage of the invention is to inexpensively provide phase shift and time delay functions by shaping of the arrays such that these functions do not require more expensive forms of electronic signal processing.

An object of the invention is to perform all the functions now implemented with materials such as optical glass, with added flexibility that comes from ability to configure channels by physical arrangement, switching, and all forms of electronic signal processing.

A capability to position primary and secondary arrays in arbitrary positions is an advantage of the present invention. Not only can arbitrary fixed positions be arranged, the input sampling surface can be in motion and be flexibly coupled to an output surface. Primary and secondary surfaces are interchangeable to provide a reverse process.

A particular benefit of wavefront transformation is to enable simultaneous delay and summation of signals that can occur in the wave propagation process. The invented device arranges the wave propagation process to establish an analog device where all the desired delays and the summation functions for a large number of focused beams are simultaneously provided by unrestricted wave propagation. In large aperture systems, such an analog device is vastly more efficient than the digital electronic equivalent that would require a massive number of digital phase shifting channels and summing operations.

DETAILED DESCRIPTION OF THE PREFERRED EMBODIMENTS

The channeled wavefield transformer is first discussed as a general concept utilizing two arrays that are both two dimensional arrangements of transducers. Transformation rules are explained. Then discussed are capabilities for parallel and simultaneous forms of transform operation and for signal modification in channels. Application with two dimensional arrays is then discussed in reference to a forward propagation device. General principles and wide applicability are made apparent by discussion of an application that involves one dimensional arrangements of transducers. The one dimensional system is readily extendable to a two dimensional form by application of these principles. It is intended to teach the basic ideas of the invention to any person skilled in signal processing, whether in optics, radar, acoustics, sonar, ultrasonics, industrial inspection, seismic prospecting, manufacturing processes, or other fields yet to be imagined that involve wavefields. Such persons will be able to extend the present invention to their field based on the examples and discussion. Such extensions will involve appropriate scaling and necessary variation of transducers and other signal processing devices to suit purposes in the different application technologies.

Figure 1:
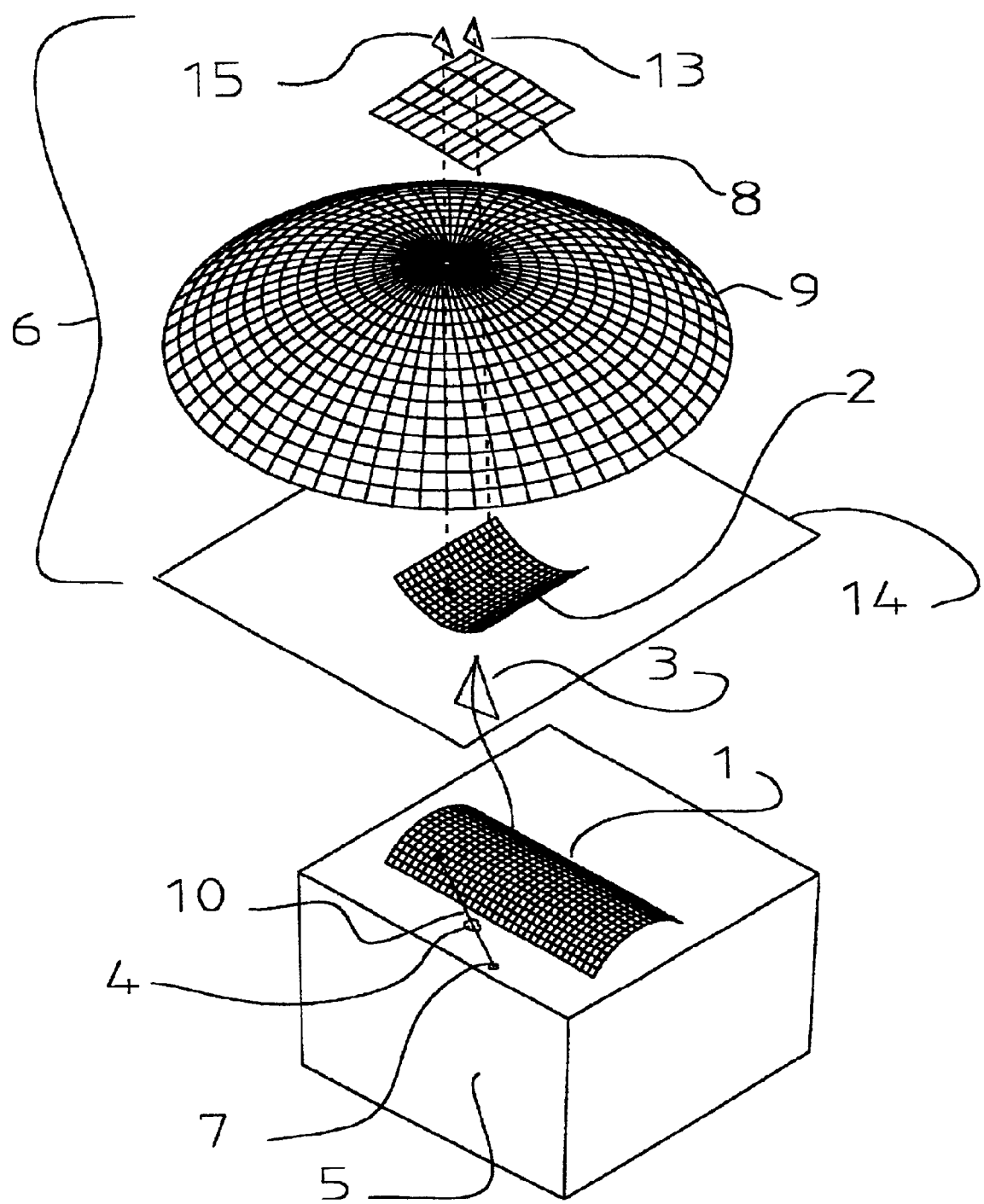
FIG. 1 shows a wavefield transformation device that enables forward propagation. A spherical output wavefield is a response to an input wavefield that is arbitrary in direction and curvature. A planar output wavefield propagates simultaneously. Wavefronts and transducer array surfaces are shown by wire frame representations.

FIG. 1 shows a part of an ultrasonic system that is a forward propagation system. The forward propagation system utilizes a channeled wavefield transformer that is defined in FIG. 2. A sensing array forms an input surface 1 where spatial samples of an input wavefield are sensed. A transmitting array forms an output surface 2 that produces an output wavefield. The output wavefield includes a spherical wave indicated by a spherical shape 9 and a planar wavefield indicated by a planar shape 8. In the forward propagation system, the planar wave arises from an intended source location 7 and the spherical wave arises from a distorting object 4 that is not at a position that can be anticipated. Thus the propagation direction 10 and curvature of the arriving wave at the input surface 1 are arbitrary. The output wavefields propagate along parallel axes 13,15 in a clear medium 6. This application involves sensing the spherical waves to determine corrections that compensate for the distorting objects of the distorting object 4. Both waves come through the transformation process at the same time in superposition. A container 5 represents natural tissue that includes distorting objects. Forward propagation is in a separate container that holds the clear, homogeneous medium 6. This separate container containing a clear medium 6 is represented by its base 14.

Figure 2:
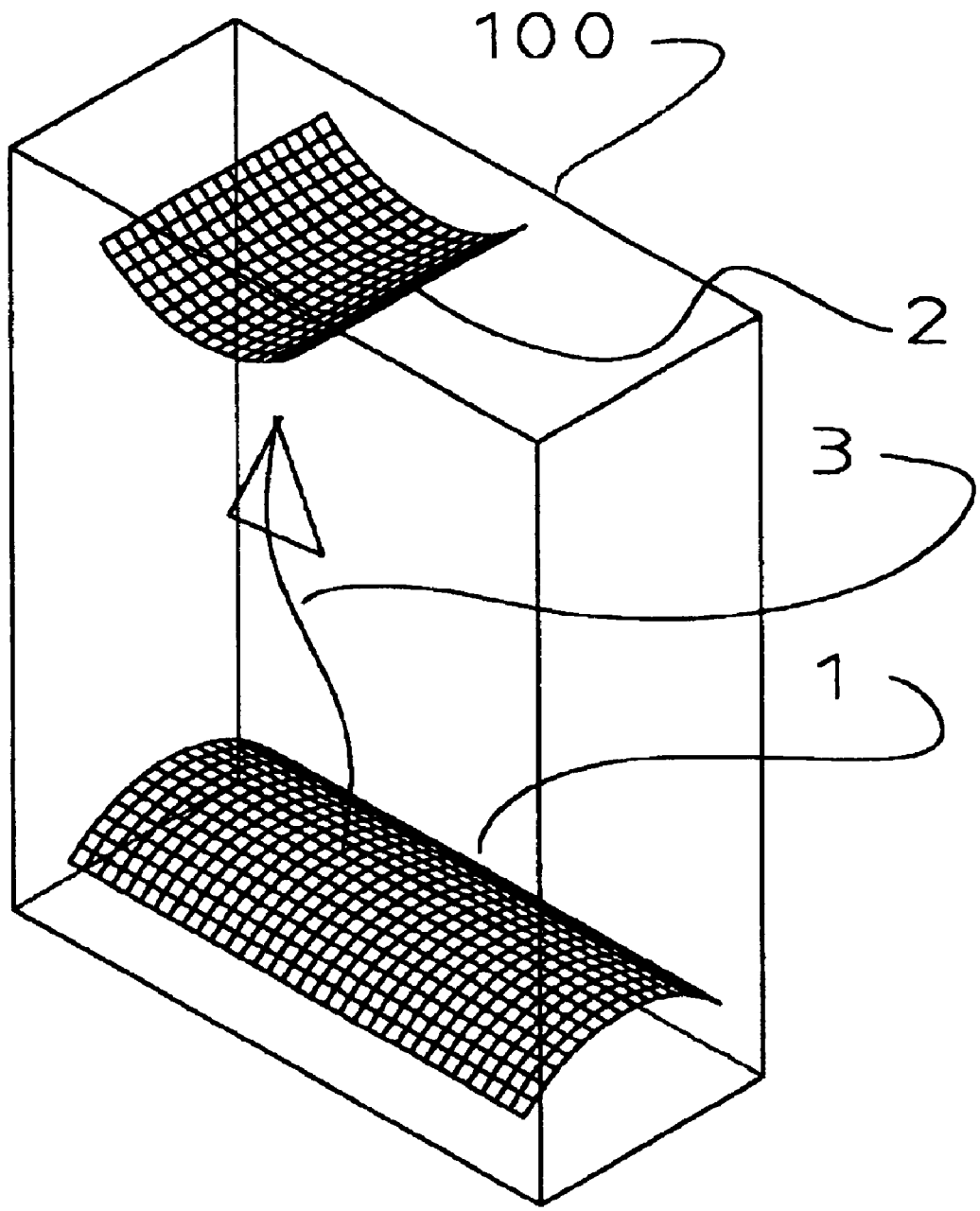
FIG. 2 shows two transducer surfaces and the interconnecting system that form the wavefield transformer.

In FIG. 2 the box 100 defines the parts of a general purpose channeled wavefield transformer. Sensing of wavefields is carried out with sensors that are distributed over input surface 1. This is also called an input array 1. Transmitting of transformed wavefields is caused by collective operation of transmitting devices that are distributed over output surface 2. This is also called an output array 2. A system of channels is indicated by the arrow 3. The channels convey phase and amplitude from the sensing devices to output transmitter devices.

Figure 3:
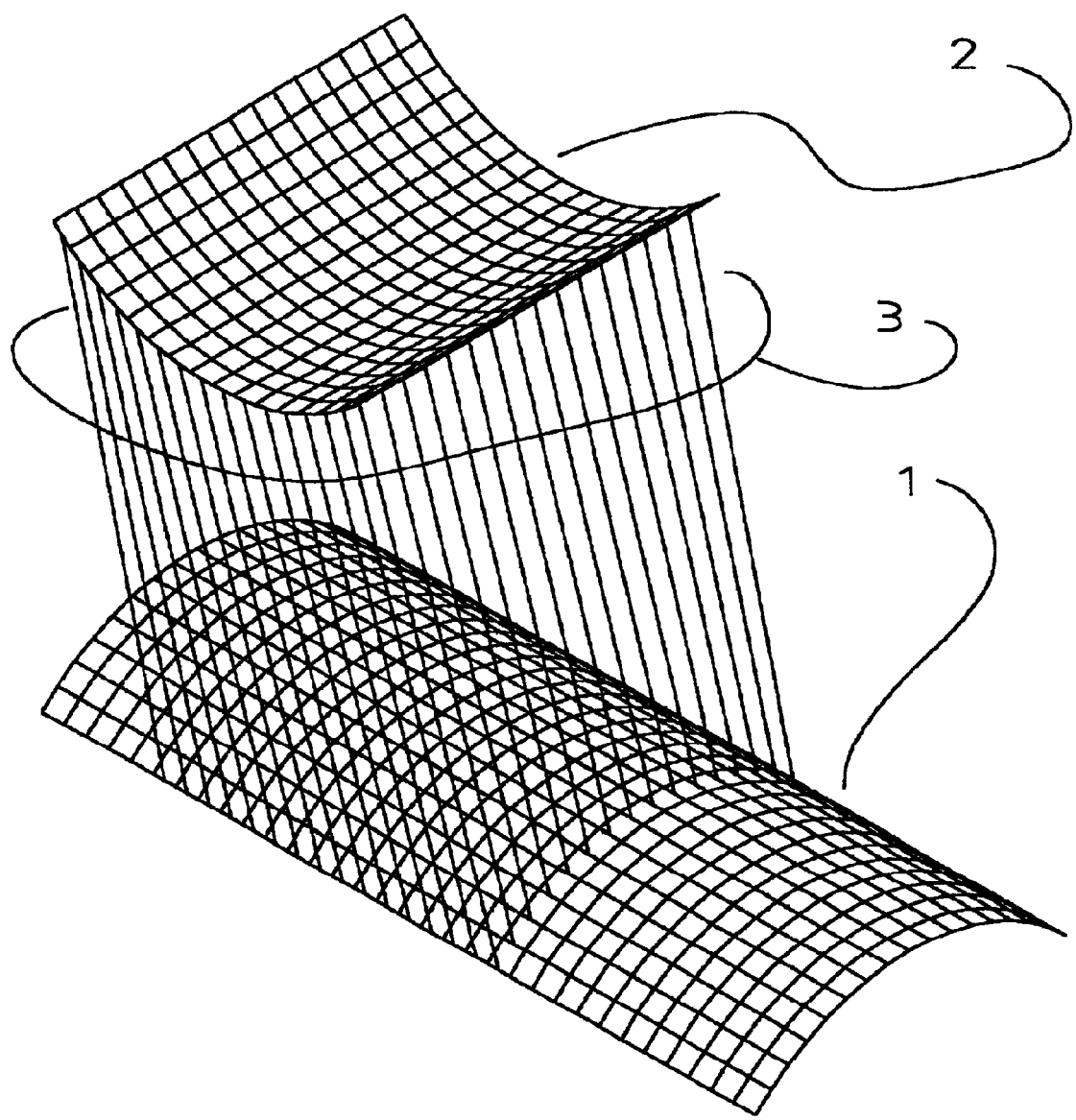
FIG. 3 shows channels arranged to carry out a one-to-one mapping.

FIG. 3 shows how one-to-one mapping channels are arranged in a simple configuration. Each channel path represents a communication operation. The communication process may also include signal processing. The collection of paths 3 defines the system of channels. A path can be a simple wire that acts as a transmission line or it can be a much more involved process. In this example only a section of an input array 1 is utilized at a given time. A later topic will address switching to rearrange channels to utilize the other parts of the input array. Channels shown are indicative of sensing and output positions that are distributed over the two dimensional input and output surfaces 1,2.

Figure 4:
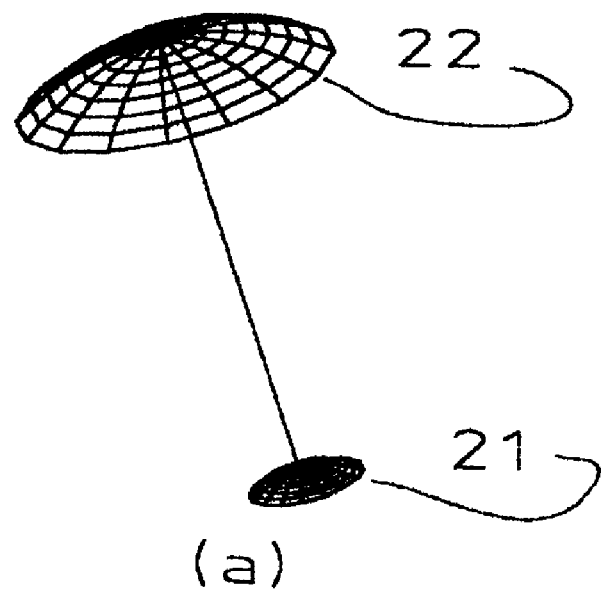
FIG. 4(a) illustrates successive wavefronts for a wavefield that propagates in a medium.
FIG. 4(b) illustrates a transformation effect, which causes a change in curvature of the emerging wavefront.
Figure 4:
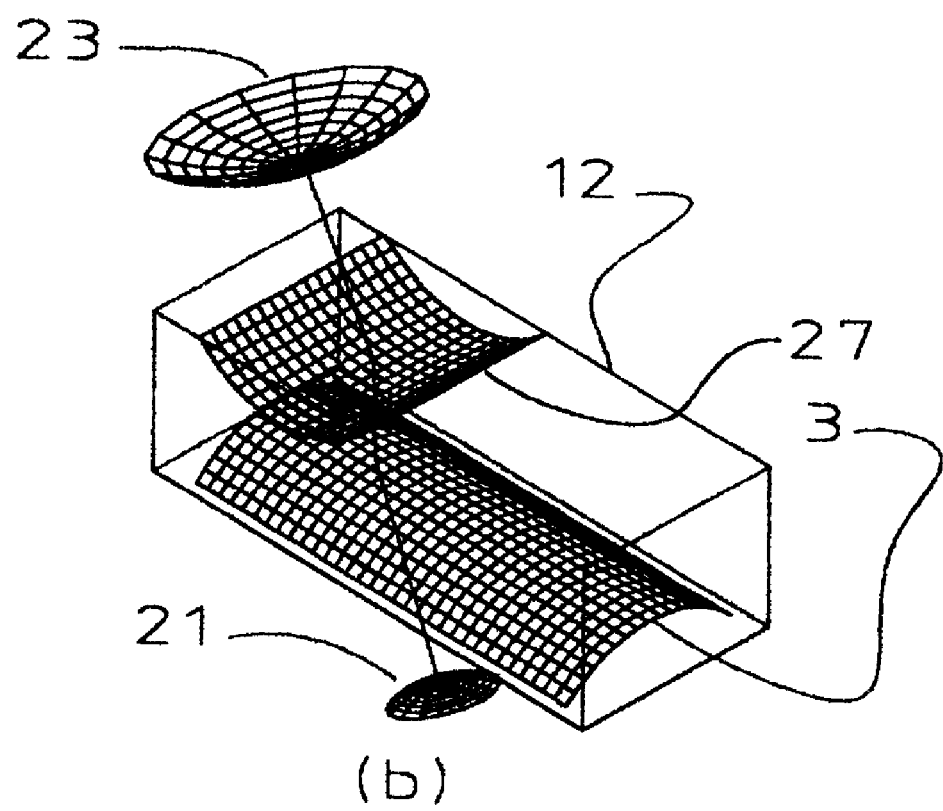

FIG. 4 demonstrates an effect of a channeled wavefield transformer. A spherical wave is shown (a) propagating in a clear medium where it operates according to spherical spreading rules such that an early wavefront 21 develops into a later wavefront 22 as a simple result of propagation effects. The transformation effect is shown (b) where the same early wavefront 21 now develops to a point where it is sensed by the input array. The operation of the transformer shown 12 is to produce an output wave represented by a wavefront 23 that has an inverted shape. Such an output wave will converge to a point, unlike the spreading wave 22 that was not transformed. The input wave originates at an arbitrary point in space such that the angle of arrival at the transformer is arbitrary and the radius of curvature of the arriving wavefront is arbitrary. The transformation thus is carried out for input waves that have arbitrary spatial characteristics. The input wave is coherent since it can be meaningfully represented by a wavefront surface.

Figure 5:
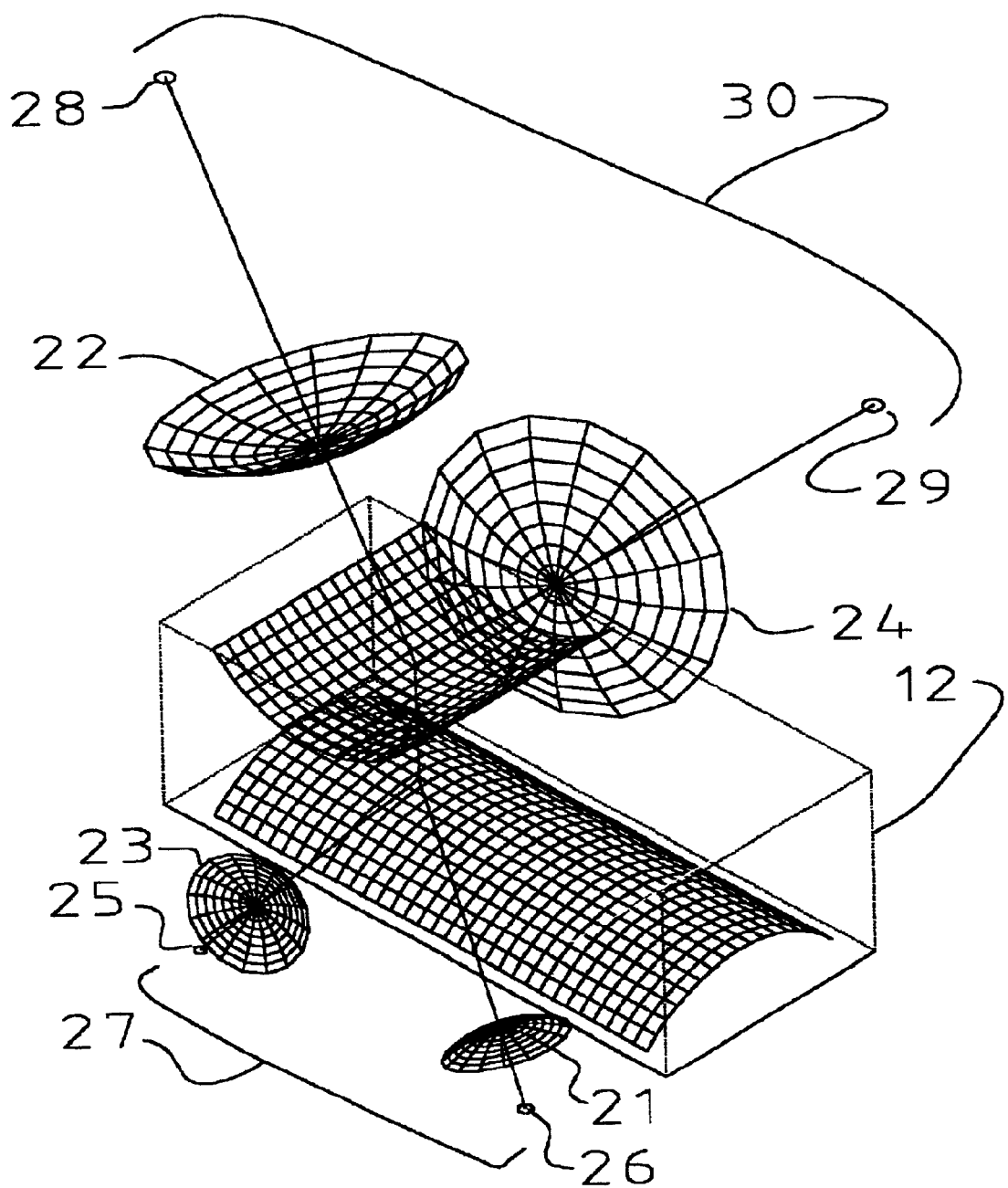
FIG. 5 illustrates two wavefields undergoing transformations in superposition to enable parallel operation.

FIG. 4 is a much simplified case since natural environments actually involve an unlimited number of waves traveling at random. Many of such waves are insignificant in amplitude. However, a system must often operate with many waves that are not insignificant. In some cases all but one wave are to be rejected, but quite commonly there are many simultaneous waves that are useful to the operation of the system. FIG. 5 shows just two waves arriving at the same transformer 101 at approximately the same time. In addition to the wave previously shown as a wavefront 21, a second wave is here shown as a second wavefront 23. The system must be designed such that superposition applies through the transformer such that simultaneous transformations will take place, as required to properly carry out a complete spatial transformation of the entire input wavefield. This is accomplished by maintaining linear processes in the sensing devices, communication channels, and output devices.

In the illustration of FIG. 5 the waves originate at points 25,26 that are located in a focal region 27. The output waves shown focus at points 28,29 in a focal region 30. Scale of the illustration of FIG. 5 is distorted to describe the process. In actual practice it is difficult to achieve focal regions that are as large as those illustrated. Simultaneous operation over significant focal regions is a common, basic function of optical lenses that is here approximated by the wavefield transformer. This example applies without restriction as to the form of wave energy involved.

Figure 6:
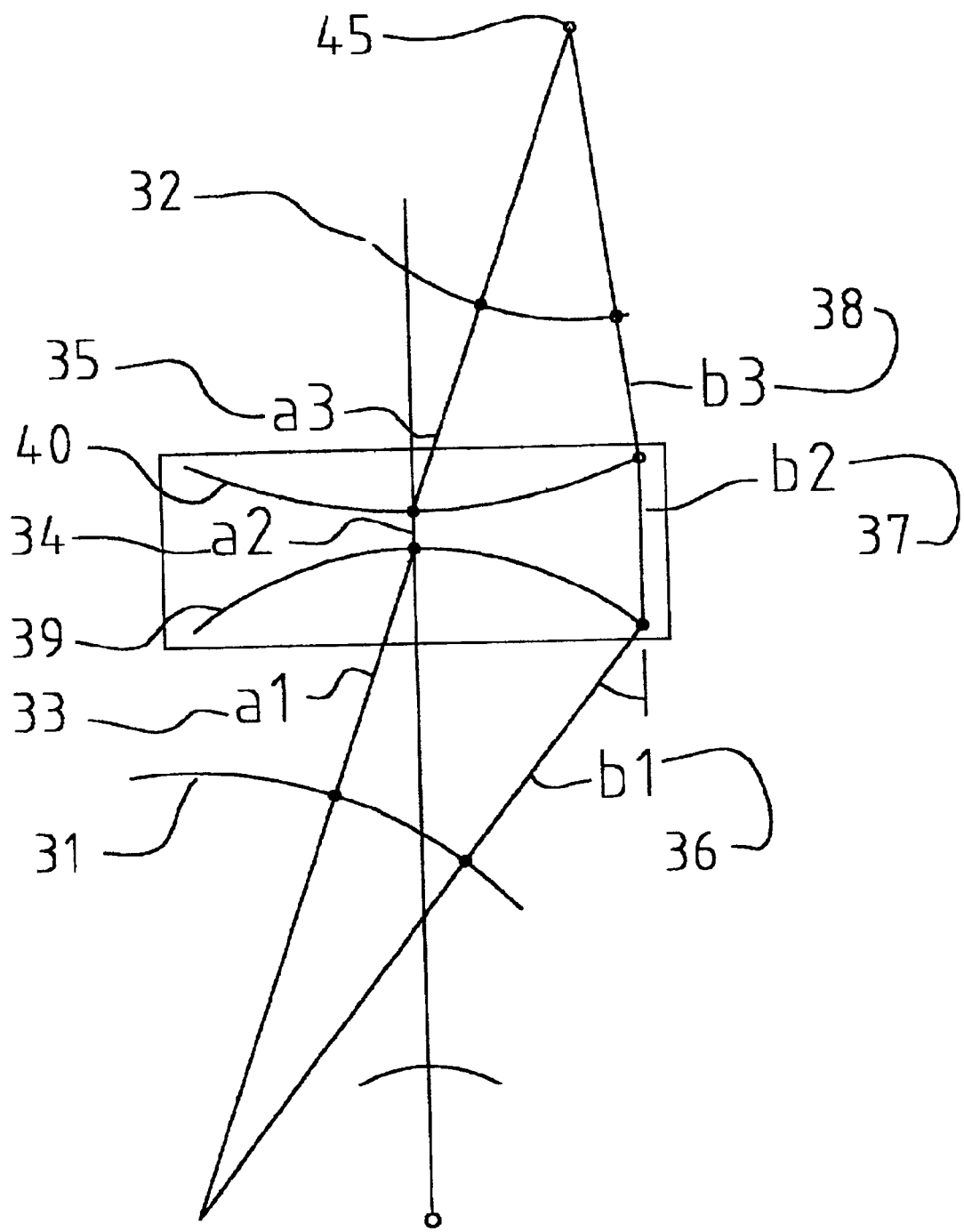
FIG. 6 illustrates geometric paths that define a transformation that reshapes wavefronts where propagation speed in channels is comparable to propagation speed of wavefields.

The transformation rule is discussed in relation to a simplified diagram of FIG. 6. The rule is much the same as that used for designing optical lenses, except the refraction effect is modified. The difference is what happens in paths a2 34 and b2 37. The design requirement is to create a wave having wavefront shape 32 as a response to an input wave having wavefront shape 31. To achieve the desired shape 32 for input shape 31 it is necessary that travel time over paths a1, a2, and a3 33,34,35 is equal to travel times over paths b1, b2, and b3 36,37,38. This rule applies for paths through all channels. Shaping of the input and output surfaces 39,40 is the simplest way to provide appropriate time adjustments while many other functions can be readily incorporated into the channels. Propagation time in the channels is a critical part of the design.

Figure 7:
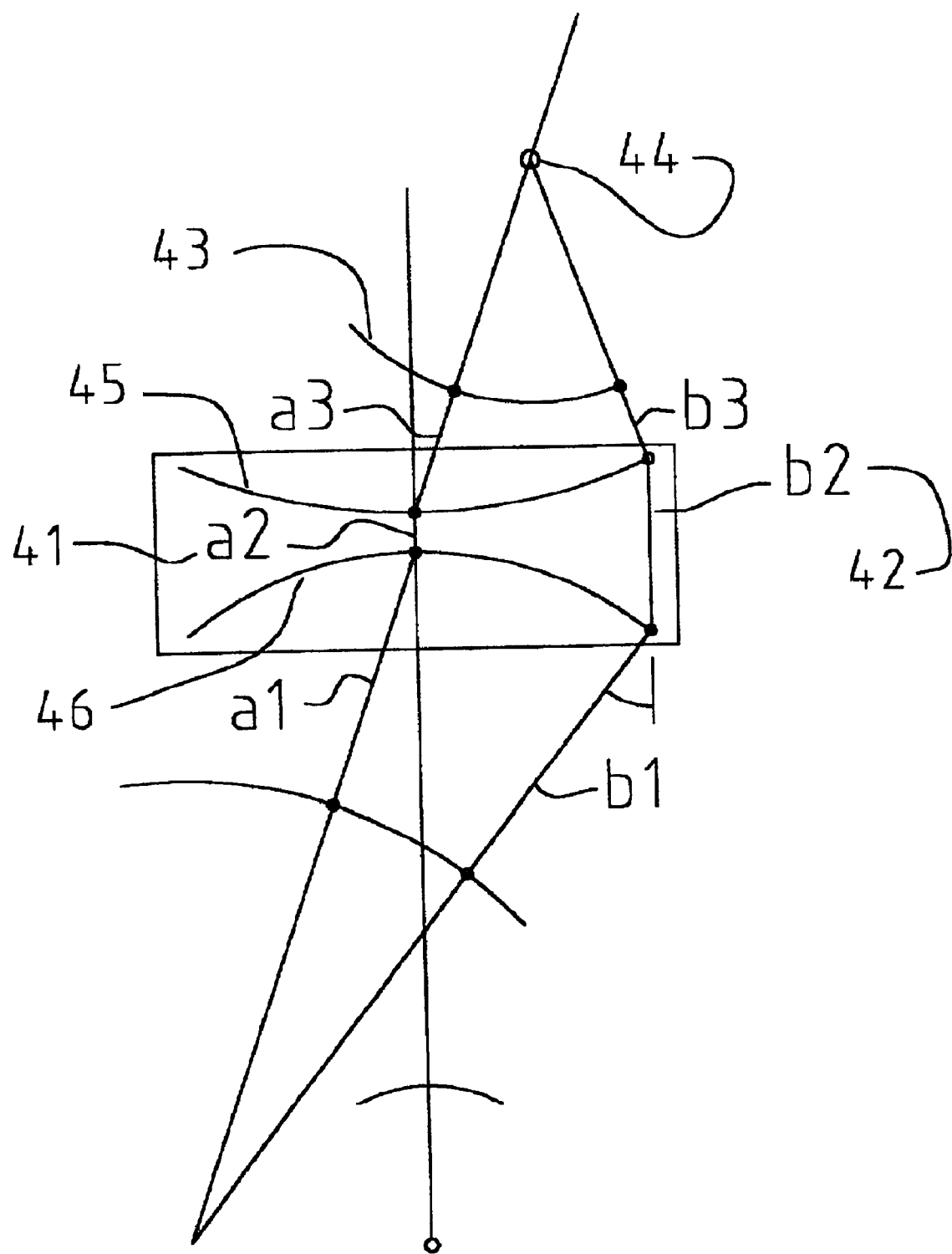
FIG. 7 illustrates geometric paths that define a transformation that reshapes wavefronts where propagation speed in channels is much faster than propagation speed of wavefields, such that time in channels can be neglected in designing the transformer.

FIG. 7 shows the benefit of electronic channels where the wavefields are ultrasonic forms of energy. In this case the paths a2 and b2 41, 42 cause a negligible travel time so the surface shapes 45,46 alone determine wavefront curvature 43. As shown, the focus 44 is at a shorter distance in FIG. 7 than is the focus 45 in FIG. 6.

Figure 8:
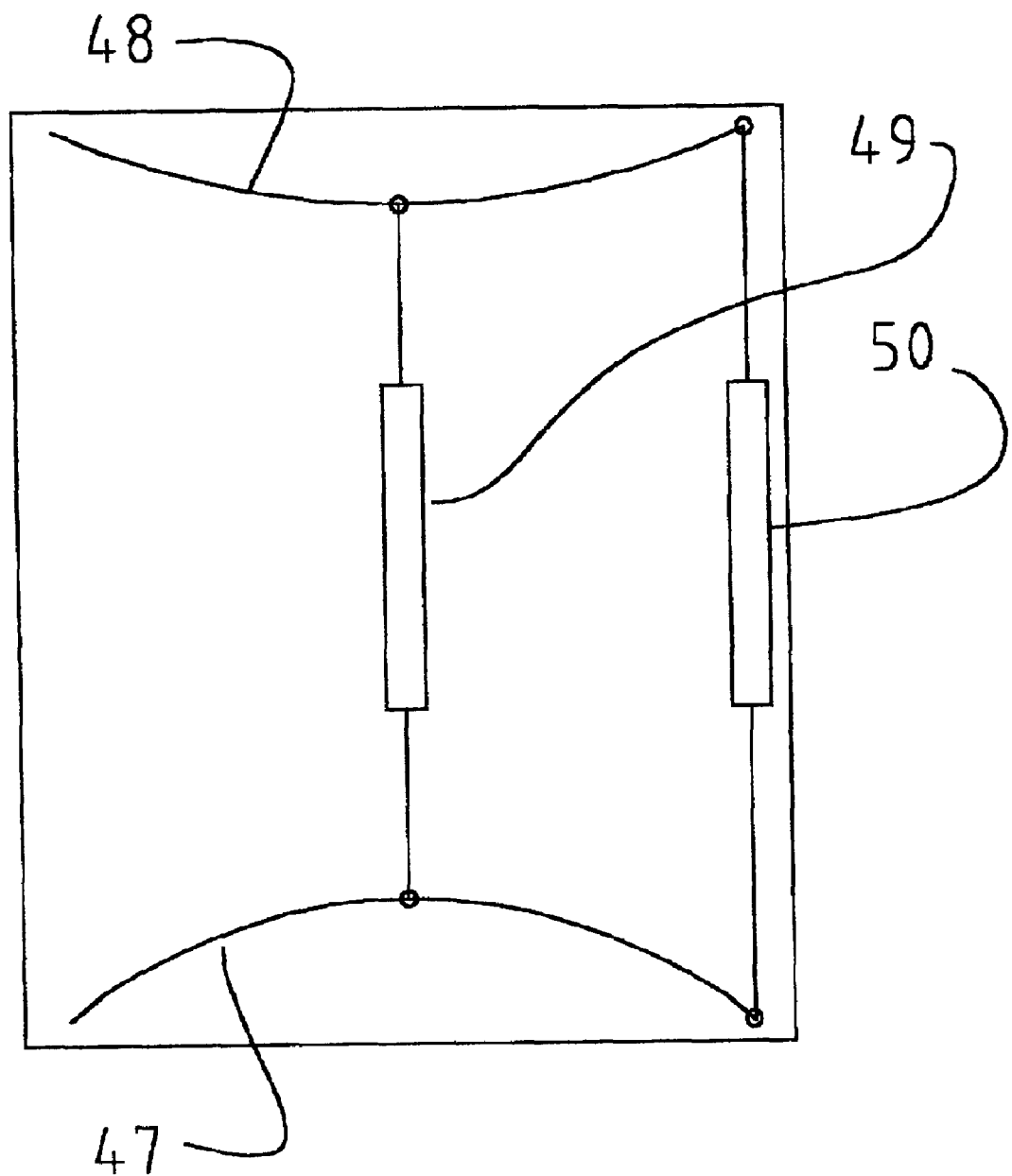
FIG. 8 indicates signal processing in two channels that are representative of many such channels required for the mapping process.

FIG. 8 shows blocks 49,50 that are functions inserted in the channels that connect from an input surface 47 to output surface 48. Two blocks in two channels are shown to represent many such blocks and channels. These blocks represent passive or active transfer functions that transform an input signal into an output signal within a channel, where all the channels operate together to control the spatial transformation that is performed on an input wavefield. Blocks 47,48 represent the entire extent of signal sensing, signal processing functions, and output device technology, including analog or digital, continuous or discrete time sampled signals. Filters, mixers, amplifiers, analog to digital converters, digital to analog converters, storage devices, delay lines, digital delay lines are examples that represent this extensive field of electronics. Such devices can be integrated into packages with sensing devices or output devices or circuit boards that hold the channel system hardware.

Figure 9:
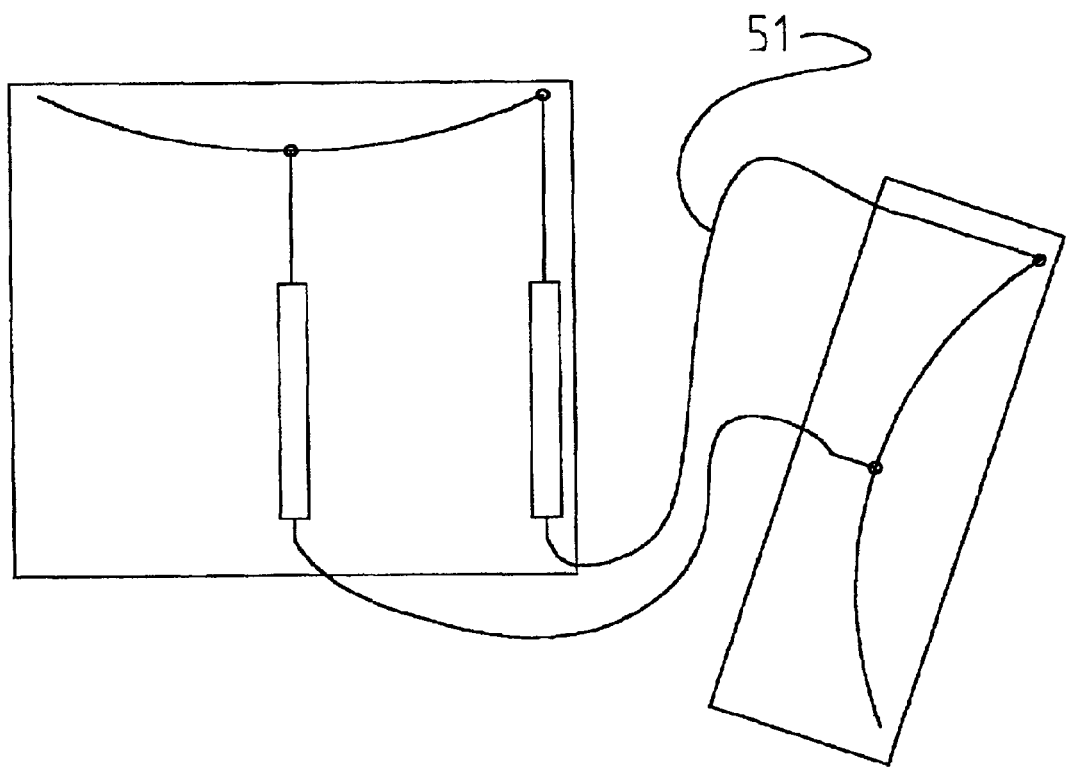
FIG. 9 indicates a capability for geometric flexibility of the channeled wavefield transformer.

FIG. 9 indicates the general flexibility of the channel system that enables a large class of functions that would require a very complicated arrangement of rigid optical devices. This figure is meant to relate to general devices that include optical ultrasound, radar devices, and many other possibilities where each field has its counterpart systems.

Figure 10:
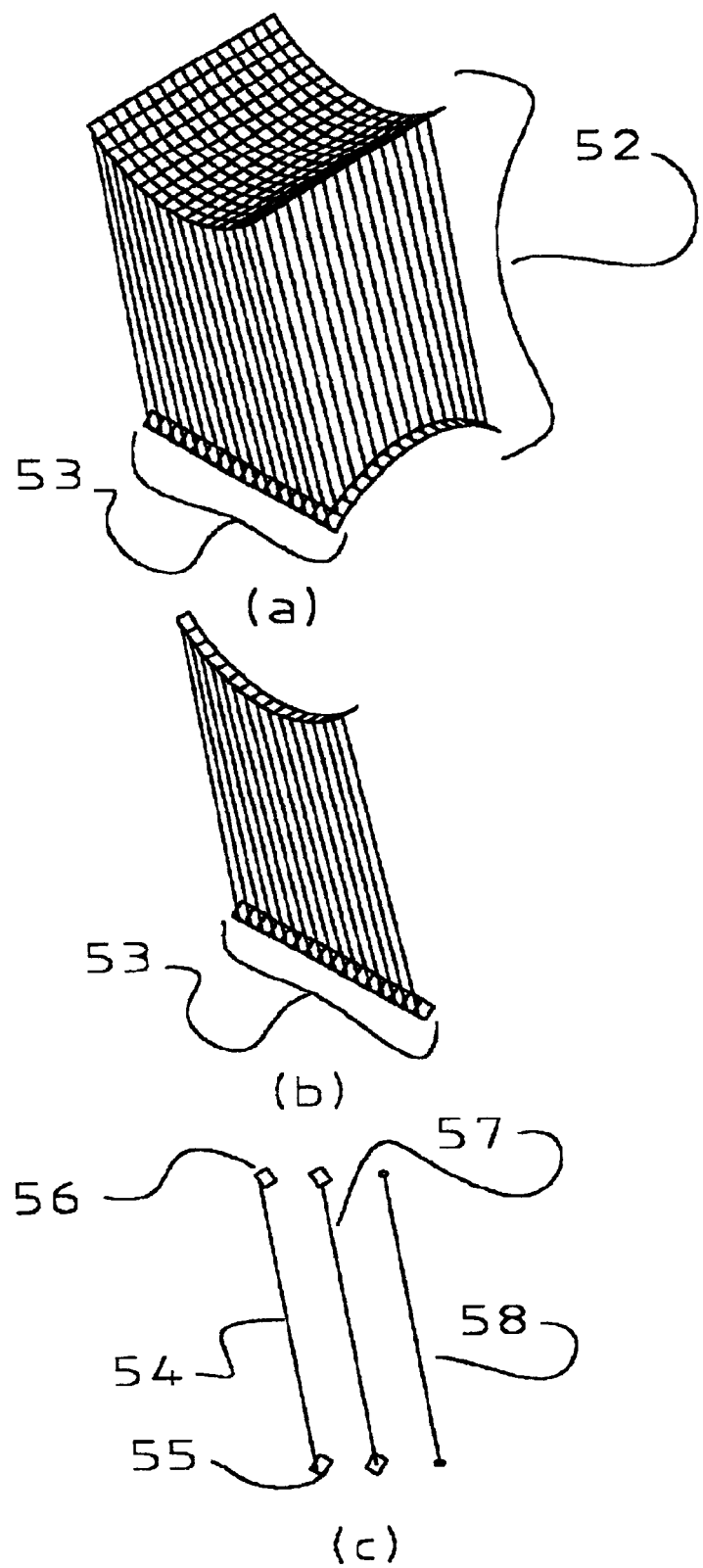
FIG. 10 shows separation of (a) a wavefield transformer into modular components. One type of module is (b) a layer that is a row of channels with attached transducers. Another type of module is (c) a single channel with attached transducers.

FIG. 10 shows how the full set of connections of (a) 52 is many layers of connections like the one layer shown below (b) 53. The single layer (b) 53 is many single connections like the one single connection shown below (c) 54. The single connection is shown as a single wire that is directly attached to the edges of the input device 55 and the output device 55. Also shown in FIG. 10(c) is a variation where connection to devices is at the center of the devices. The devices are small rectangles that are approximately flat surfaces. This small surface shape can be a factor in operation of the device. A needle like form 58 with bead like devices at each end is a way to implement each channel with input and output devices that are more like point devices where device shape is no longer an issue. An attractive feature of the needle form is that complicated surface shapes can be formed by stacking the required number of needles, and sliding them in the stack such that the points form a surface. The same concept applies to the layer of channels (b) 53. A modular assembly in the form of a card would be formed with one dimension of the desired surface shape formed as the card edge. A stack of cards is then formed to the final surface shape by appropriately sliding the cards.

Figure 11:
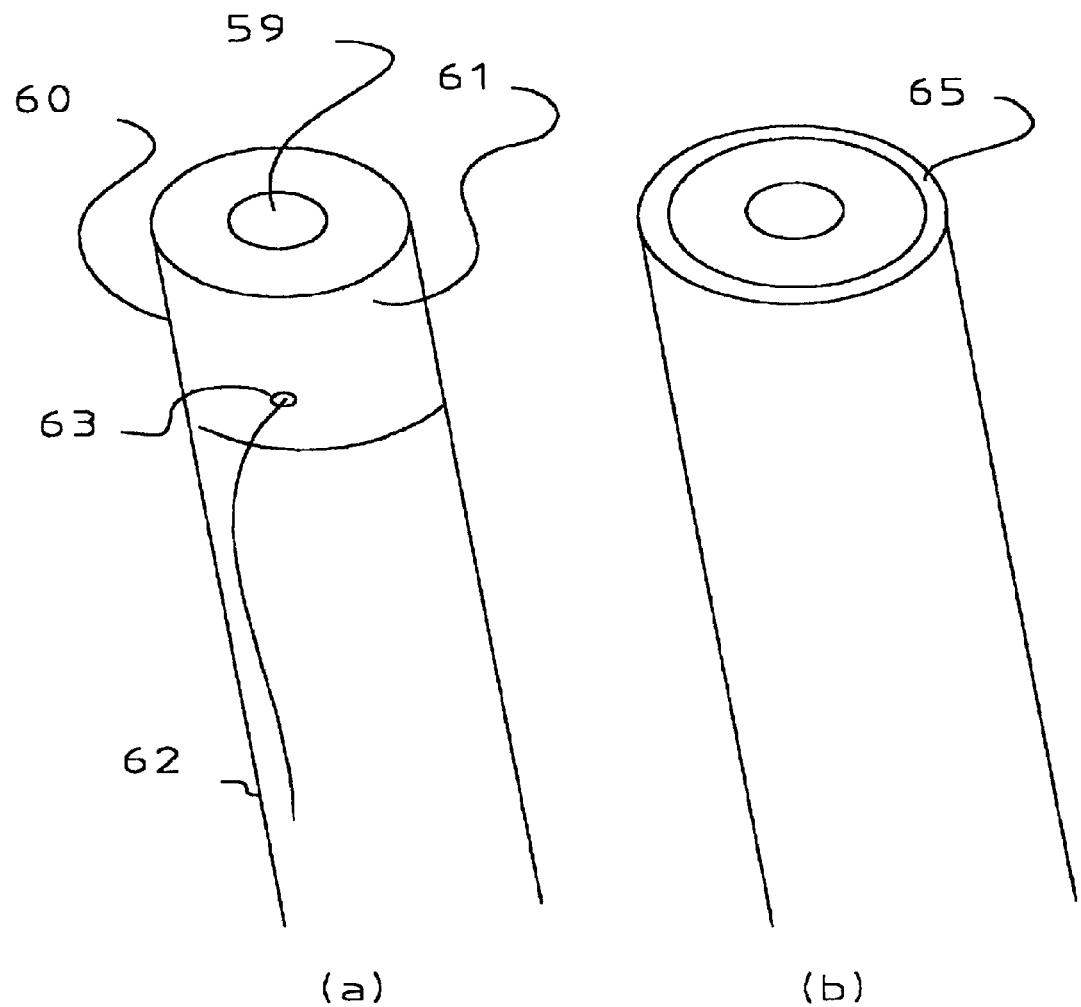
FIG. 11 shows a thin, needle like, tubular transducer module that represents a single channel with attached transducers.

A module that is a needle design is shown in detail in FIG. 11. An inner part is shown (a) having a core conductor 59 that is one lead wire around which is formed a bead like piezoelectric cylinder 60 of barium titanate that is poled radially. Thin metalization 61 is applied to the outer diameter of the cylinder. An epoxy cylinder 62 is formed below as a backing for the piezoelectric device operation and as a structural device. Wire is attached at a point 63 on the metalized surface by soldering. Also shown (b) is an insulating sleeve 65 which also functions as part of the ultrasonic wave generating process. The insulating sleeve 65 is formed of glass microballoons in an epoxy binder. Not shown is a cut-out for the lead wire. One form of transformer is simply a set of needles with transducers on each end where needles are cut to size to give the right shape of surfaces when needles are stacked. More practical alternates involve a separate stack of needles for each surface with wire conductors connecting respective needle modules.

Figure 12:
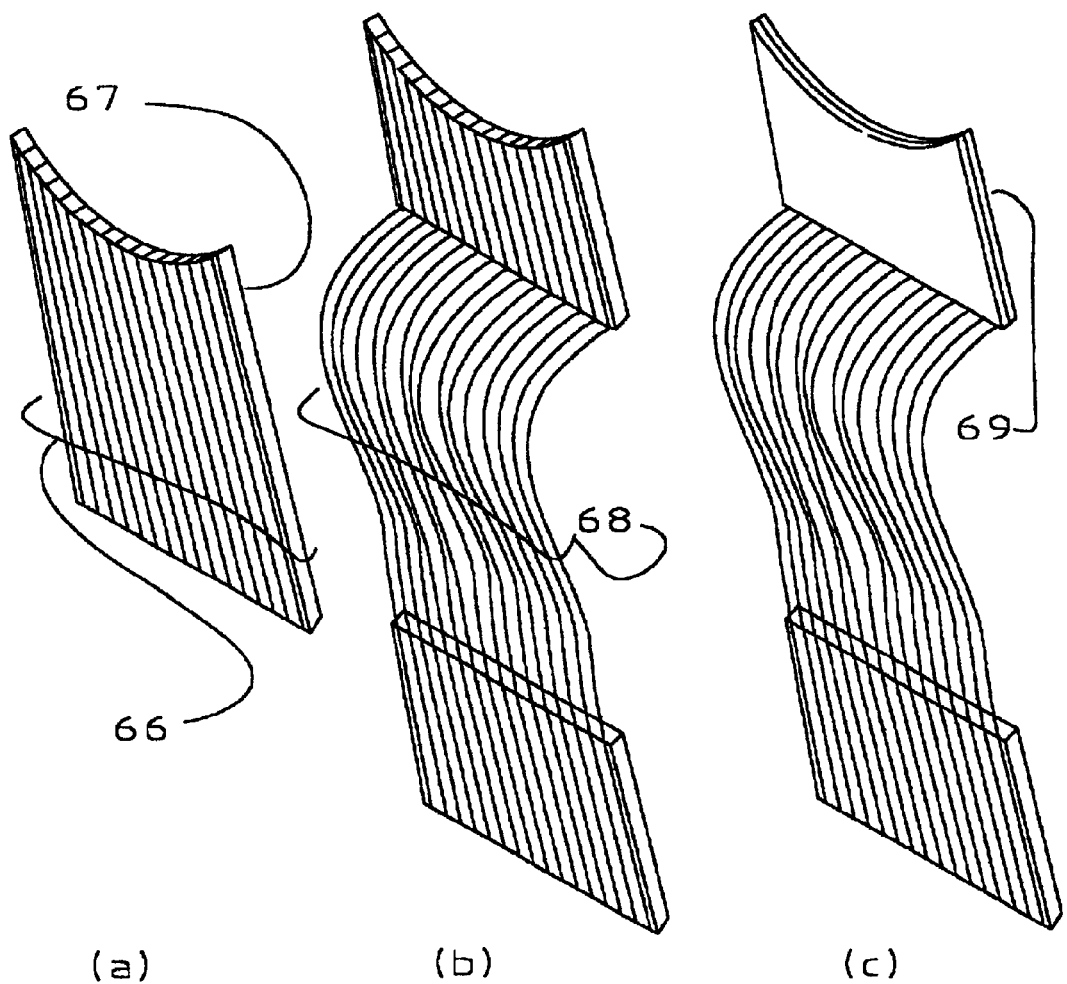
FIG. 12 shows (a) a single layer module that is constructed as a flat card with a curved edge, where transducers are on both a straight edge and a curved edge. (b) shows separation of the card into two parts with a flexible cabling that connects the parts. (c) shows one of the cards as a sandwich form with transducers forming a thin strip on the curved edge as an example of both conventional and sparse spatial sampling.

An alternate is a card module based on the layered form of FIG. 10(b). This alternate is shown in FIG. 12. In FIG. 12(a), connections 66 are made between respective input and output elements of the layer on a printed circuit card 67 that also provides backing and mounting for the rectangular transducers. A variation shown in FIG. 12(b) is to split the card to allow independence of input and output surfaces, where flexible connections 68 complete channels between cards. FIG. 12(c) shows a variation 69 where a thin card as before is now sandwiched between isolating cards. By making the basic card very thin, a strip of transducers is produced, which would actually be formed by dicing a continuous strip. By cutting away all but small pieces, point elements could be formed which perform similarly to the needle module devices.

Modular assembly has significant economic advantages. A module is considered to be a working assembly of a transducer and necessary connections that can be manufactured as a unit. Mass production of modules is then possible. The modular nature allows assembly in a system by relatively simple means. This is especially important here where complicated surfaces are needed, where these can be formed by stacking modules. It is desirable that the modules be readily connectable to cables of many wires.

Operating principles are demonstrated by applications that follow. Where one dimensional arrays are shown, it is intended that the principles are applicable to two dimensional arrays.

Figure 13:
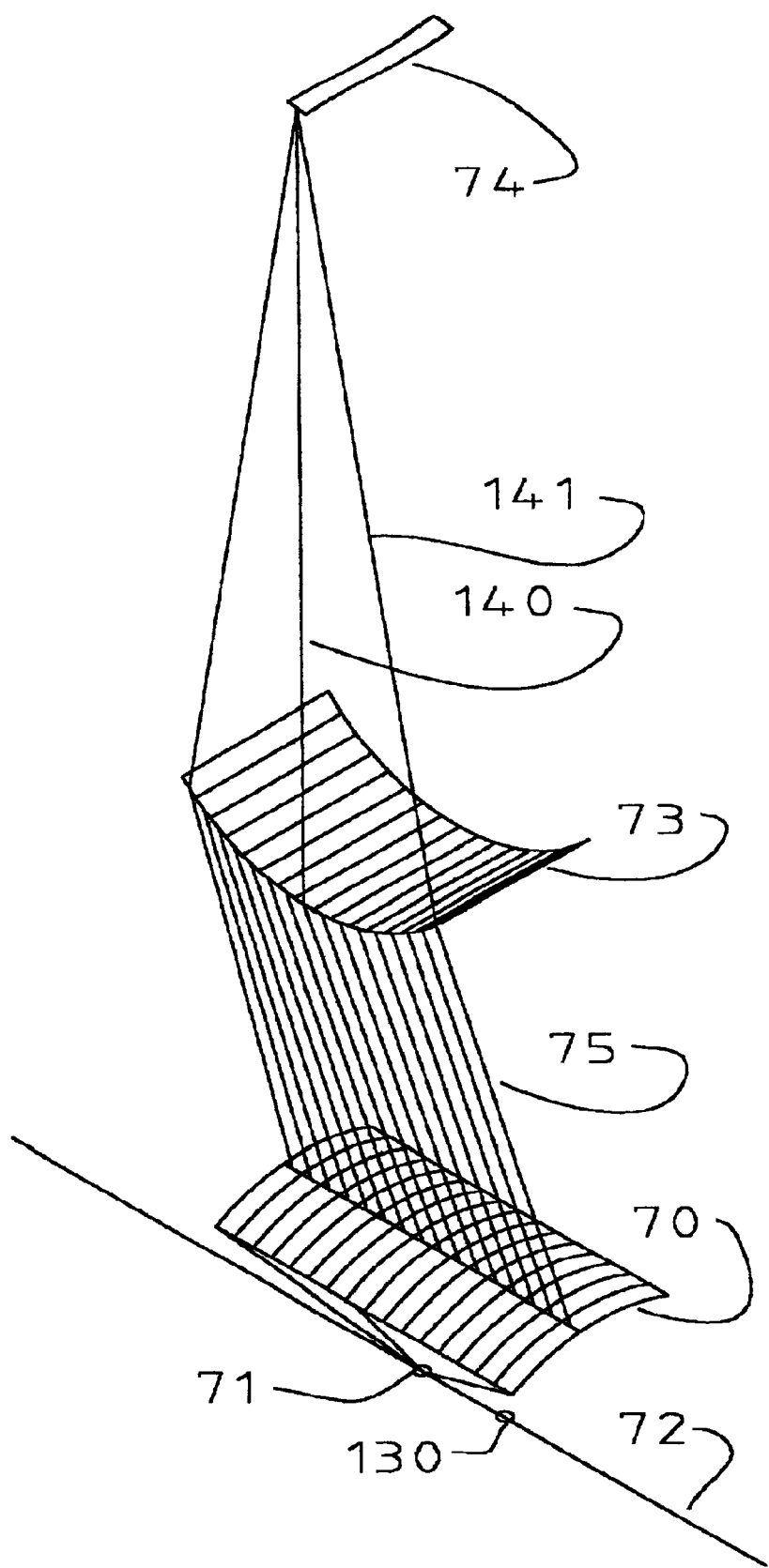
FIG. 13 shows a wavefield transformer that involves one dimensional arrays that have substantial area due to width of the transducer elements, where focusing for a cylindrical array is accomplished by the transformation.

FIG. 13 shows an ultrasonic receiving system example using one dimensional arrays. These form two dimensional surfaces, but the arrays involve elements that are arranged along a straight line and a curved line. The width of the elements causes the surfaces to be two dimensional. A cylindrical array 70 of arc strips is focused at a point at the center of a small sphere 71 along the axis 72 of the cylindrical array 70 by the action of the wavefield transformer. The curvature of the secondary array 73 of straight strips causes outer paths 141 to be shorter than the center path 140 to compensate for the mismatch between cylindrical waves that arrive at the cylindrical array. The result is a focus over a single element transducer 74 that collects energy related to energy from the focus point 71. Channels 75 include amplifiers that raise signal power, but physical path length is of no practical concern. Gain of amplifiers is broadly uniform with slight taper to minimize sidelobes. The system shown operates for distributed sources from within a small, fixed sphere 71. Dimensions of this sphere are established by the resolving effects of the aperture formed by the input surface. The wavefield of interest has a spatial form that is approximately known, though the amplitude and phase of the wave system, as a unit, are variables.

Figure 14:
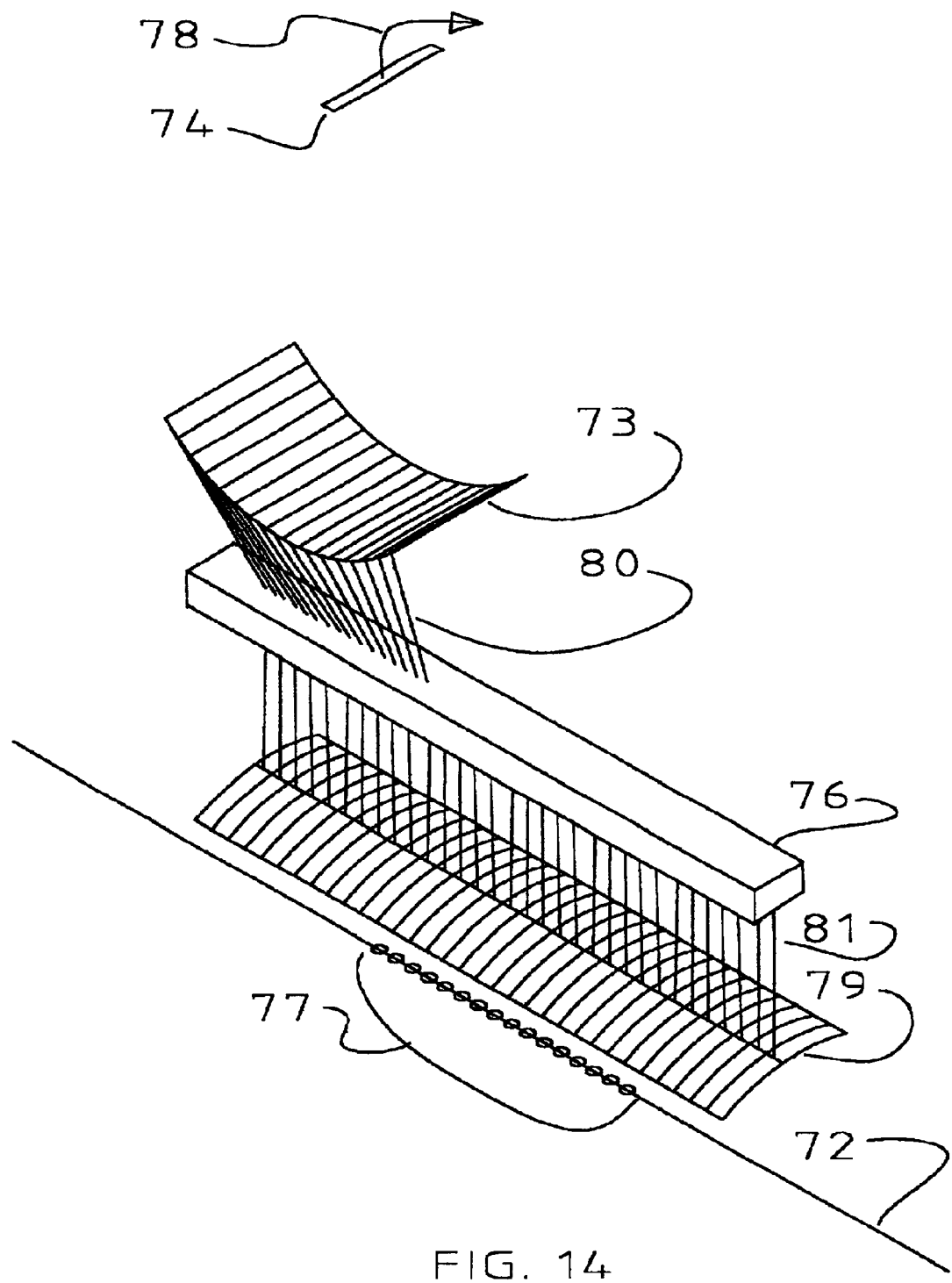
FIG. 14 shows incorporation of a switching system that allows changing of the transformer configuration so as to focus at a sequence of stepped points on the cylinder axis.

FIG. 14 shows a much longer cylindrical array 79 of arc shaped strips with the same curved array 73 of straight strips. A switching system 76 is inserted between the two arrays that reconfigures the transformer by connecting paths 80 to different respective paths 81. This serves to move the focus point to various positions 77 along the axis line 72. The various focus points are thus sequentially sensed by the energy collecting transducer 74 which is the source of signal 78 for the receiving system shown. This all can be reversed to form a transmitting system.

Figure 15:
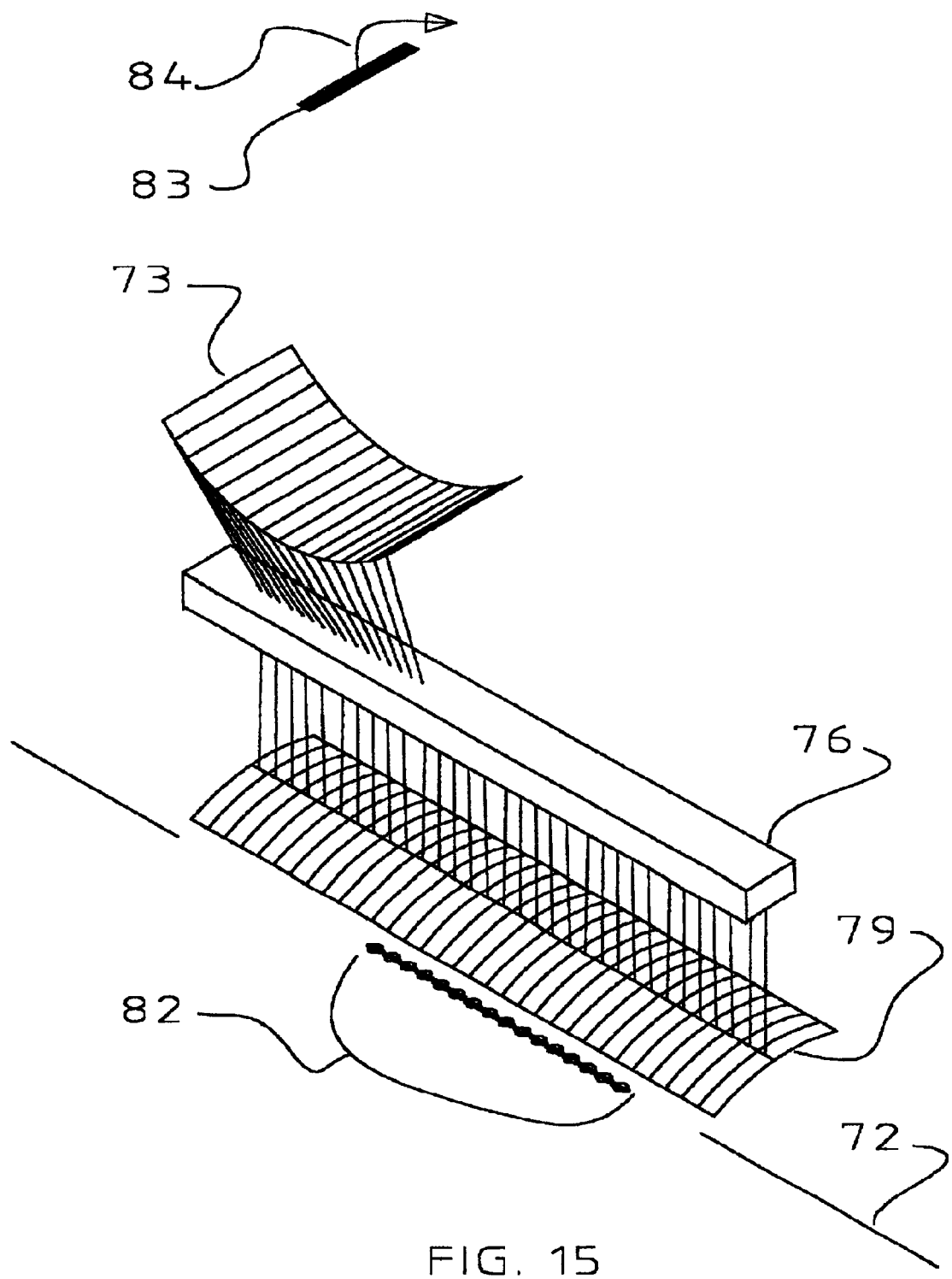
FIG. 15 indicates a vernier resolution arrangement that allows imaging multiple points in a limited focal region about each stepped point onto multiple transducers in an output focal region.

FIG. 15 shows a similar system except a vernier resolution capability is added. This means that for each step that the switches cause, a finer scale of resolution is possible with the added features shown here. Multiple points 82 are now selectively sensed along the same axis line 72. This is enabled by multiple collecting strip transducers 83, which provide a set of separate output signals 84. These outputs are capable of parallel or sequential use by a system that has multiple output systems or a selecting switch that goes to a single output system. Accomplishing the vernier resolution with only the switching channel switching system 76 would require many more cylindrical strip elements and much more complicated switching. Reversibility to operate as a transmitting system is again possible, except that for parallel operation, a method of separable transmit signal codes would be required to resolve the outputs along the axis 72.

Figure 16:
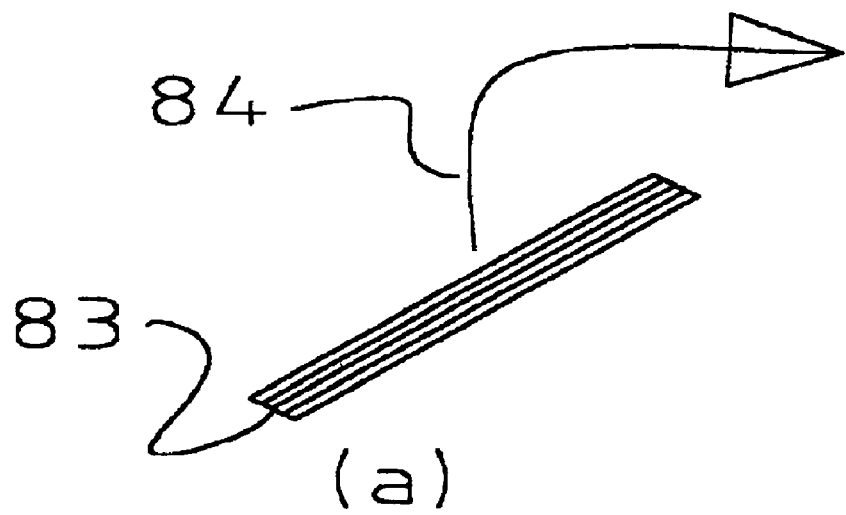
FIG. 16 shows vernier resolution focal regions as expanded views.
Figure 16:
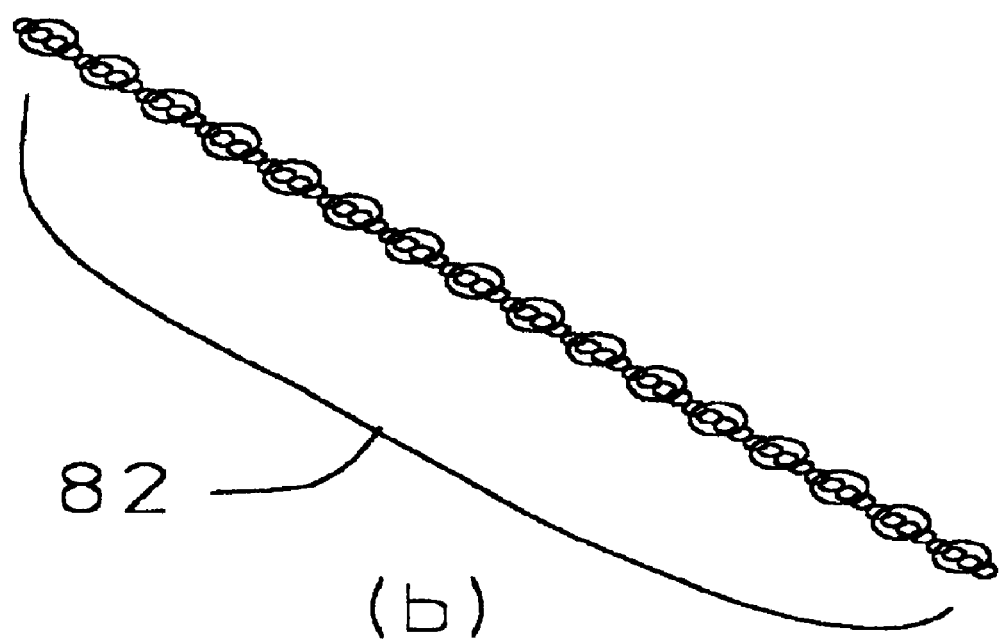

FIG. 16 provides clarification of the previous figure. Vernier resolution is indicated by the smaller circles in (b) of this figure. These small circles are representative of square like cells. The larger circles represent actual resolution cells that are rectangular that have a smaller dimension that is the same as the square side. Multiple collecting strips are visible (a).

Figure 17:
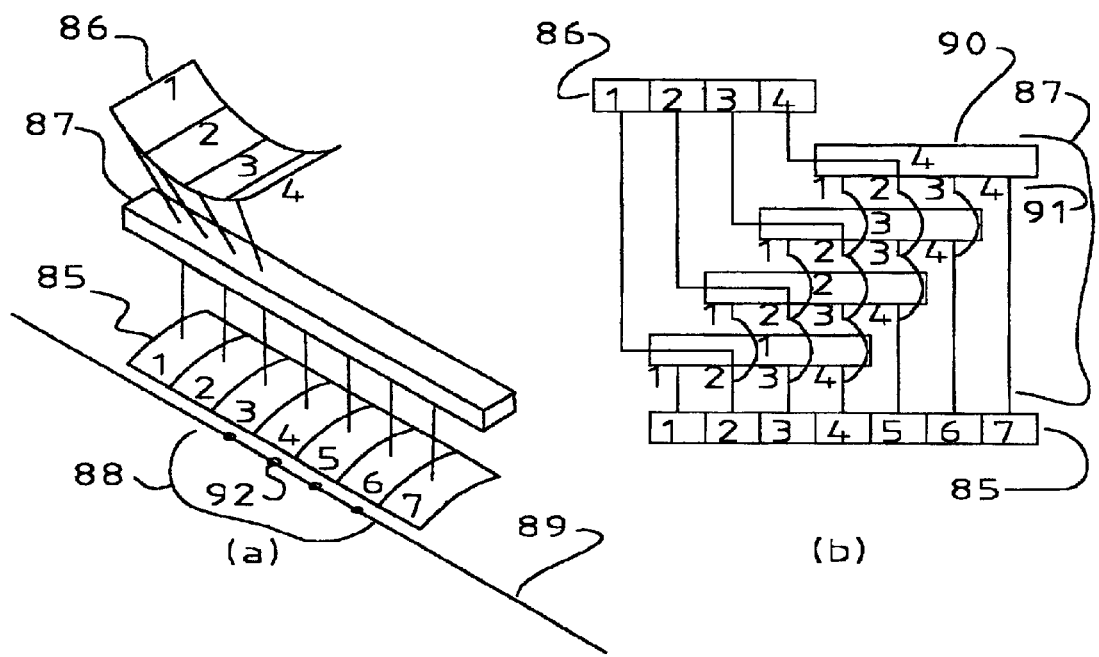
FIG. 17 shows the one dimensional switching mechanism with a simplified example that can be extended to larger systems including those that involve two dimensional surfaces.

FIG. 17 gives guidance in design of the switching system 76. For practical reasons the switch system 87 that is here detailed only for an eight element version 85 of the previously discussed long cylindrical array 79 that connects to a four element version 86 of the other array 73. These are called the primary array 85 and the secondary array 86 in respect to the discussion of this figure. FIG. 17(a) is a pictorial view and FIG. 17(b) is a corresponding, simplified electrical schematic. The number of switches in the switch system 87 is equal to the number of elements in the secondary array and the number of switch positions is equal to the number of focus points 88 along the axis. Each switch has one pole that can be connected to multiple switch positions. For the simplified diagram there are, thus, four switches 87, where each switch has four switch positions 91. There are seven elements in the primary array 85. The switches modify the mapping channel assignments to select a desired focus point. For the second focus point 92, the switches are all set as shown to their contact position number 2 so the one-to-one mapping is from primary elements numbered 2,3,4,5 to respective secondary elements numbered 1,2,3,4. All the switches operate like switch number 4 90 where contacts 91 numbered 1,2,3,4 are selected by digital logic control that is not shown in the diagram. Such switch systems can be formed with industry standard, high speed CMOS logic parts 74HC4351 where such parts provide an eight position switch device. If more contact positions are needed, multiple 74HC4351 devices can be grouped to form larger switch units, with appropriate logic control. Although not shown, the use of amplifiers in such a system would be obvious to a circuit designer.

Extension of the model of FIG. 17 to operate with a two dimensional sensing array involves a set like that shown for each row of transducers and a set like that shown for each column of transducers. Switch devices can be integrated into packages such as the cards shown in FIG. 12.

Figure 18:
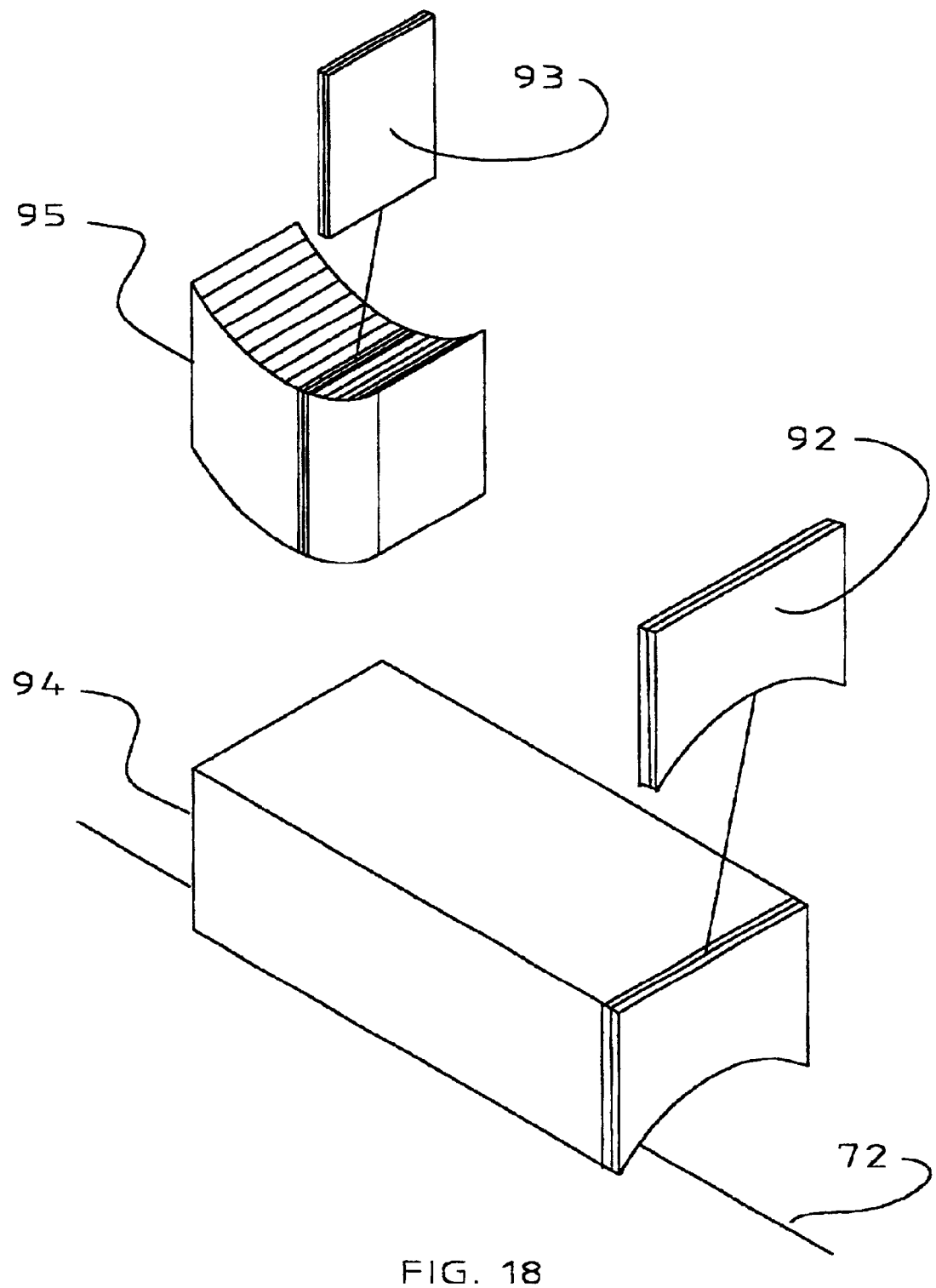
FIG. 18 shows how transducer arrays are formed as stacks of transducer card modules having strip transducers on a card edge.

FIG. 18 shows how the large system is assembled based on the previously discussed concept, where transducer array assemblies 94,95 correspond to arrays 79,73 of FIG. 15. These assemblies are constructed using modular methods that involve card edge transducer modules 92,93 with strip transducer elements. These are stacked to form the needed two dimensional surfaces of the wavefield transformer, as well as the set of collecting transducers that is not shown.

Using a bistatic method where transmit and receive directions are different, both transmit and receive systems can focus along the same axis line 72. This can be visualized as two assemblies like the long cylindrically surfaced assembly 94 shown in FIG. 18, where the second of these two is rotated about the axis 72 such that they do not physically interfere. These two arrays provide respective transmit and receive functions. Grating lobe problems can be minimized by using different spacing between cards of the long cylindrical transmit array and the long cylindrical receive array. A grating lobe causes an ambiguous focus point 130 as indicated in FIG. 13.

Figure 19:
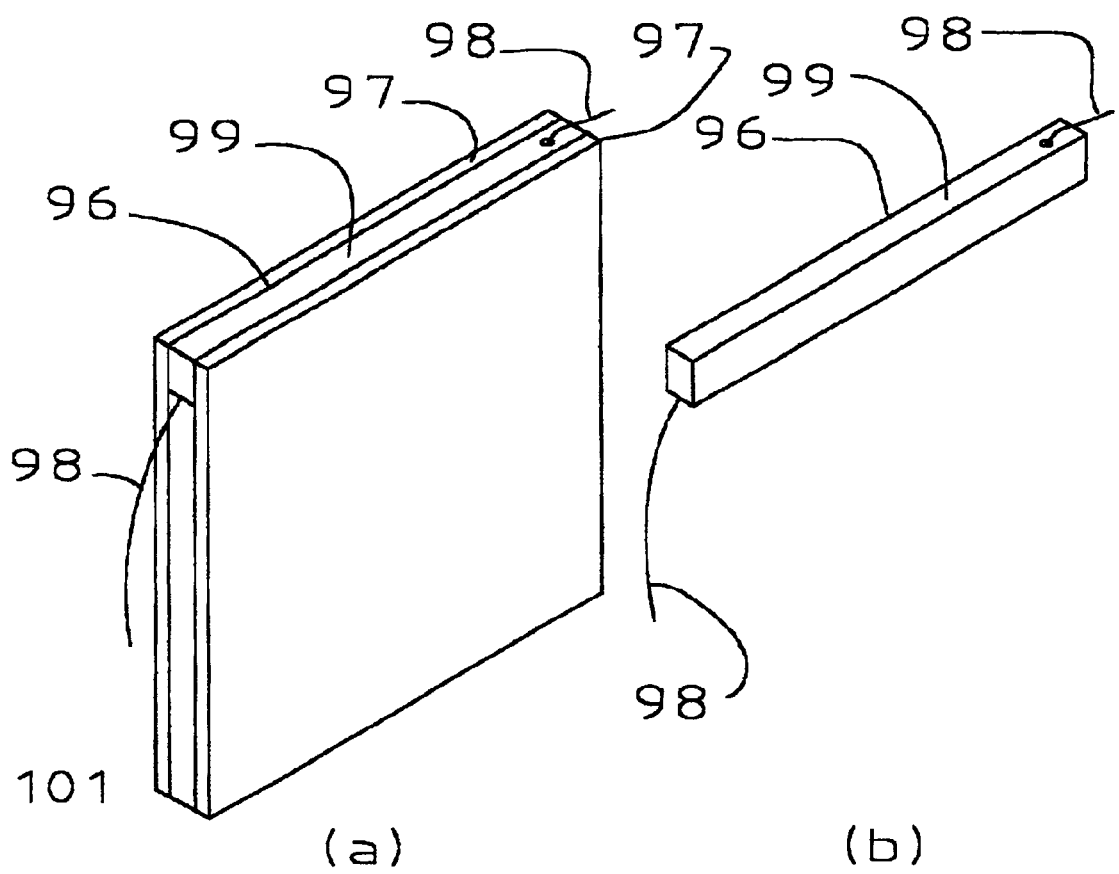
FIG. 19 shows details of a transducer card module.

FIG. 19 shows detail of a card edge transducer. An active strip is formed of a bar of piezoelectric material 96, which is shown between separating cards 97 that insulate, unclamp, and isolate the bar. Electrical connections are shown 98 where wires are soldered to metalized surfaces 99 as is typically done in building ultrasonic transducers. Backing material 101 is included between the separating cards, where such material is cured epoxy resin.

Figure 20:
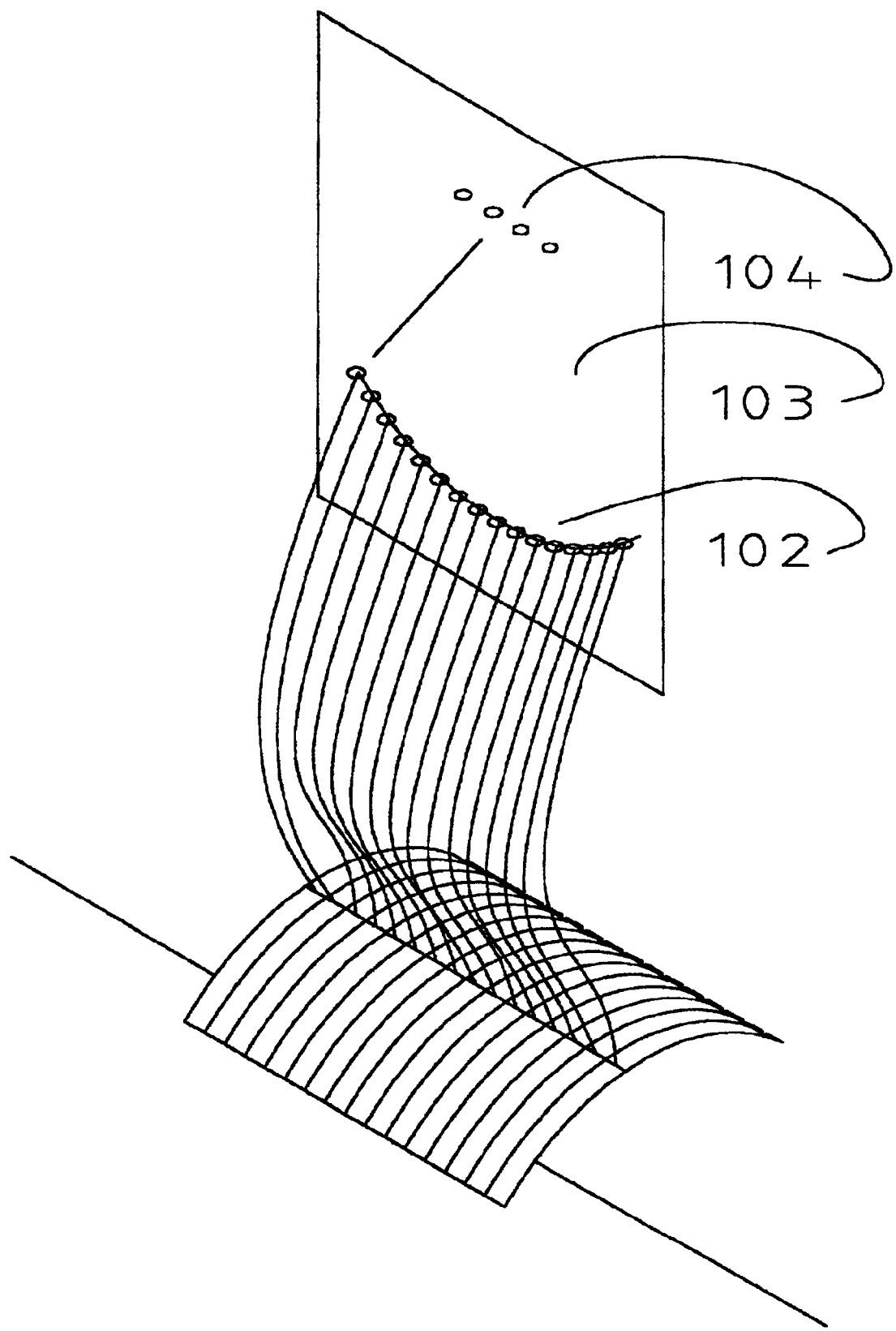
FIG. 20 shows an equivalent wavefield transformer involving a surface acoustic wave (SAW) device as the secondary of the channeled wavefield transformer.

FIG. 20 shows a variation where the secondary array is replaced with an array of transducers 102 that activate surface acoustic waves on a card 103 surface. The surface acoustic waves are collected by transducers 104 that are within a focal region for the geometry of the system. The primary wavefield is in the form of bulk ultrasonic waves and the secondary wavefield is in the form of surface ultrasonic waves. This is an example of an input wavefield that is of different form from the output wavefield. Such mixtures can involve a variety of wave energy forms.

Figure 21:
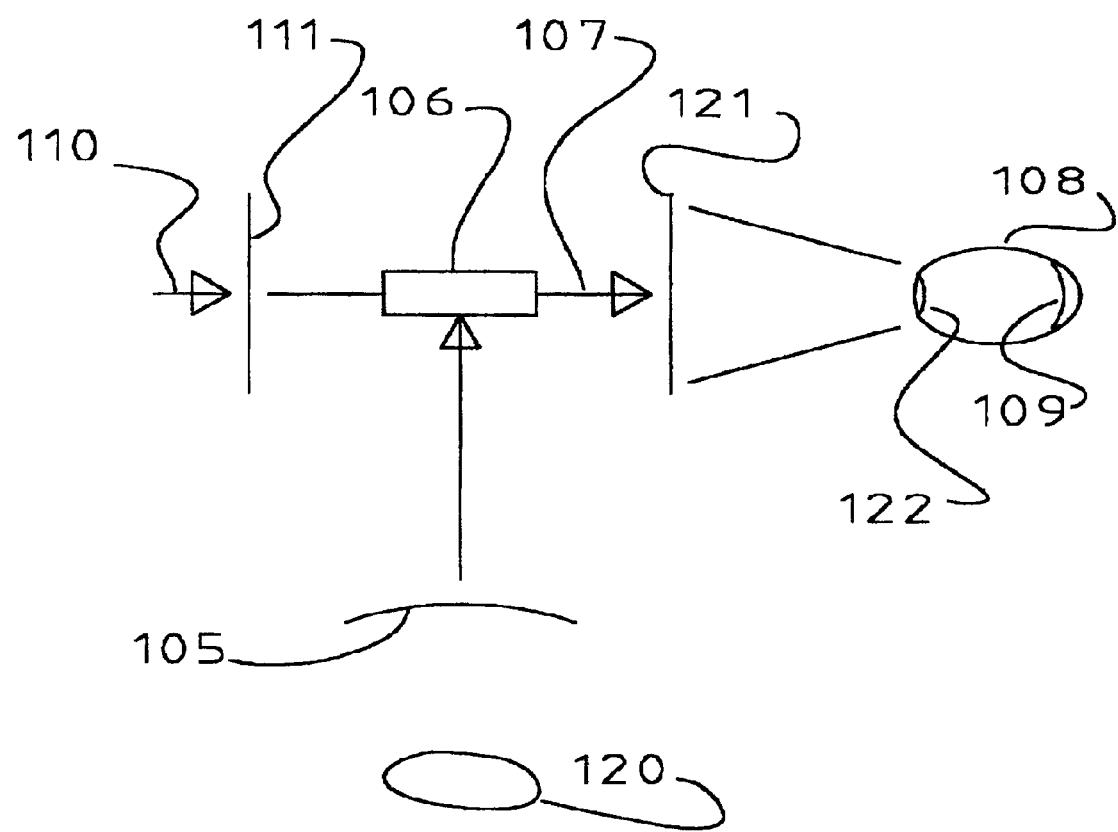
FIG. 21 shows an ultrasonic television system where ultrasonic waves are conveyed to form optical output waves that are focused in the focal region of the eye.

FIG. 21 shows an ultrasonic television system where objects in a field of view 120 are directly imaged on the retina of an eye 109. Here the primary wavefield is a bulk ultrasonic wavefield and the secondary wavefield is an optical wavefield. Signals from a two dimensional ultrasonic array 105 drive modulators 106 that impose phase and amplitude information from the ultrasonic transducers onto light signals in fiber optic lines 107. The outputs of the fiber optic lines couple at a two dimensional output surface 121 to the approximately free space medium of air and then propagate directly to a human eye 108. Shaping of the fiber optic output points and the effect of the cornea of the eye 122 provides focus onto the retina of the eye 109. A collimated laser beam 110 activates the fiber system with unmodulated wave energy through input points 111.

Figure 22:
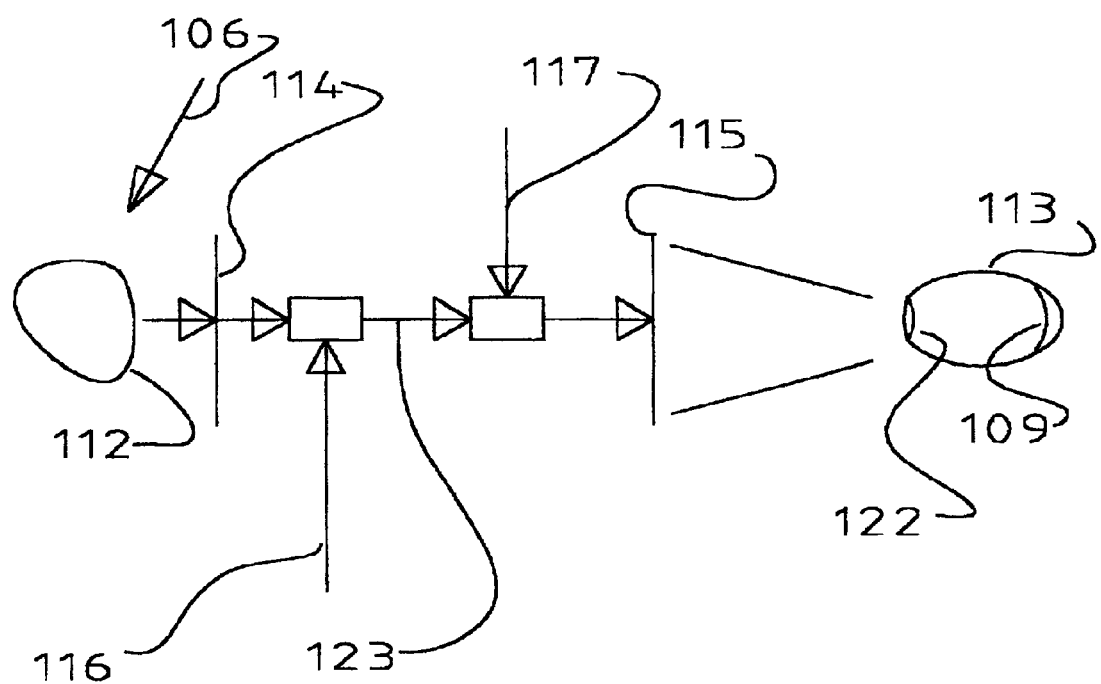
FIG. 22 shows a coherent television device where optical wave systems are conveyed to form optical waves that are focused in the focal region of the eye.

FIG. 22 shows flexibility of the channeled transformer concept where amplifiers and such devices are inserted in the lines. This produces a new form of television where coherent light from objects 112 at one location are locally received by a receiving array 114 and transferred coherently to another location to create a coherent wavefield that is focused directly into an eye 113 according to the transformation rules discussed in relation to FIG. 6. Focusing is determined by shapes of receiver 114 and transmitter 115 surfaces, together with the effect of propagation times in the channels. Coherent channels are multiplexed using a system of carrier signals 116 and demultiplexed with a similar system of carrier signals 117. By limiting the optical bandwidth of the input by using laser illumination 117 of the source object, the total bandwidth is made realizable. This must be related to capacity of the communication link 123 which may be an optical fiber, electrical transmission line, a radio frequency connection, a laser link, and other such means.

In the fiber optic systems, it is necessary to recognize the effect of the small scale details of the input and output coupling devices. Small surfaces must conform to the appropriate general surface shape, or must satisfy spatial sampling criteria. This tends to make practical realization of such systems limited to relatively small aperture devices or to other configurations where grating lobe problems can be controlled.

Given the counterparts for so many different wave energy types, it becomes necessary to cut off discussion of all the possible applications of the spatial wavefield transformer. It is clear that many embodiments will come about after considering common optical devices as guiding models. Thus it is expected that channeled wavefield transformers will implement windows, mirrors, and lenses using fiber optics as well as counterparts in ultrasound, radar, sonar. Electronically controlled windows, image reversing mirrors, variable lenses, noise cancellation, diffraction cancellation are immediately apparent concepts that would be possible based on this invention, the scope of which is defined by the following claims.

I claim:

1. A coherent transformation device for sensing an arbitrary coherent input wavefield, where said arbitrary coherent input wavefield has arbitrary spatial characteristics, where said sensing is at points that are distributed over an input surface to determine respective sensed signals, where said respective sensed signals are coherent signals that represent phase and amplitude of said arbitrary coherent input wavefield at said points, and said transformation device coherently conveys said respective sensed signals through respective mapping channels to respective output devices where said respective output devices are distributed over an output surface, and a purpose of said transformation device is to produce a coherent output wavefield in a clear medium by collective and coherent operation of said respective output devices, where said coherent output wavefield is a response to said arbitrary coherent input wavefield.

2. A device according to claim 1 where said input wavefield is an ultrasonic wavefield and said output wavefield is an ultrasonic wavefield, and said arbitrary spatial characteristics are limited to spatial characteristics of a wavefield originating within a resolved region of a pre-determined source point of an objective wavefield, where said resolved region is defined by said input surface for a given wavelength of said objective wavefield.

3. A device according to claim 1 that establishes forward propagation, where said forward propagation is a continuation of propagation of signals carried by said input wavefield.

4. A device according to claim 1 where said sensed signals are time sampled sensed signals.

5. A device according to claim 1 where said sensed signals are conveyed in channels that are virtually simultaneous channels that enable said collective and coherent operation of said respective output devices.

6. A device according to claim 1 that implements an approximation of an optical mirror effect.

7. A device according to claim 1 that implements a counterpart of an approximation of an optical mirror effect for wavefields that are not optical wavefields.

8. A device according to claim 1 that implements an approximation of an optical mirror effect except that mirror image effects are reversed.

9. A device according to claim 1 that implements a counterpart of an approximation of an optical mirror effect except that mirror image effects are reversed for wavefields that are not optical wavefields.

10. A device according to claim 1 that implements an approximation of an optical window effect.

11. A device according to claim 1 that implements a counterpart of an approximation of an optical window effect for wavefields that are not optical wavefields.

12. A device according to claim 1 that implements an approximation of an optical lens effect.

13. A device according to claim 1 that implements a counterpart of an approximation of an optical lens effect for wavefields that are not optical wavefields.

14. A device according to claim 1 where said coherent output wavefield is arranged to cancel a continuation of said coherent input wavefield.

15. A device according to claim 1 where said respective mapping channels include active devices.

16. A device according to claim 1 where said respective mapping channels include signal processing devices.

17. A device according to claim 1 where said respective mapping channels include frequency translation devices.

18. A device according to claim 1 where said respective mapping channels include switching devices that rearrange mapping connections between input devices and output devices.

19. A device according to claim 1 where propagation time in said respective mapping channels is negligible to shape of said coherent output wavefield.

20. A device according to claim 1 that implements a coherent television system where said coherent output wavefield is arranged to focus directly into an eye.

21. A device according to claim 1 that implements a coherent ultrasonic television system where said coherent output wavefield is arranged to focus directly in an eye.

22. A device according to claim 1 where said sensed signals are time sampled sensed signals and said output devices produce output signals are created at discrete times and with duration such that said output signals are not continuous.

23. A device according to claim 1 where input devices are also used as said respective output devices such that said input surface is aligned with said output surface, where said mapping channels provide connections between said input devices and said respective output devices.

24. A device according to claim 1 where wavefields are ultrasonic wavefields, and said device utilizes transducer assemblies that are constructed using a modular method where assemblies are stacks of parallel modules, with active elements at an end of a stack, and two dimensional surfaces are formed at said end of a stack by sliding said modules in a direction that is generally perpendicular to said two dimensional surfaces.

25. A device according to claim 1 that is a component in an aberration correction system.

26. A device according to claim 1 in a combination transmit system and receive system where transmit and receive functions focus at a common position, where number of channels is minimized by use of sparse sampling methods, and a method of reducing grating lobes by varying spacing between said points that sense said input wavefield for said receive system relative to spacing between said output devices for said transmit system, where said grating lobes are reduced by mismatch between transmit grating lobe positions and receive grating lobe positions.

27. A system that includes a coherent transformation device that senses an input wavefield at points that are distributed over an input surface to determine respective sensed signals, where said respective sensed signals are coherent signals that represent phase and amplitude of said input wavefield, and said transformation device coherently conveys said respective sensed signals through respective mapping channels to respective output devices where said respective output devices are distributed over an output surface, and said coherent transformation device produces an output wavefield in a clear medium by collective and coherent operation of said output devices, where said input wavefield includes a plurality of coherent input wavefields, and said transformation device produces coherent output wavefields in response to respective said coherent input wavefields, and said system is configured to utilize a plurality of said coherent output wavefields in parallel.

28. A system according to claim 27 where a plurality of points in a focal region are imaged at a plurality of points in a second focal region.

29. A coherent transformation device that senses a spatially coherent input wavefield at points that are distributed over an input surface to determine sensed signals, where said sensed signals are coherent signals that represent phase and amplitude of said input wavefield, and said transformation device includes a channeled mapping system that coherently conveys said sensed signals to assigned output devices where said output devices are distributed over an output surface, and said transformation device produces an output wavefield in a homogeneous medium by collective and coherent operation of said output devices, where said output wavefield is a spatially coherent response to said spatially coherent input wavefield, and said channeled mapping system includes devices that provide active signal modification.

30. A device according to claim 29 where said channeled mapping system provides a one-to-one mapping.

31. A device according to claim 29 where said output wavefield is a high powered output wavefield, such that power intensity of said high powered output wavefield is sufficient to modify materials.

32. A device according to claim 29 where travel time of signals through said channeled mapping system has a negligible effect on said output wavefield.

33. A device according to claim 29 and a switching system to modify said channeled mapping system.

* * * * *